United States Patent
Ferrari et al.

(10) Patent No.: US 12,011,483 B2
(45) Date of Patent: Jun. 18, 2024

(54) LIQUID DELIVERY COMPOSITION

(71) Applicant: COSMO TECHNOLOGIES LTD., Dublin (IE)

(72) Inventors: Franca Ferrari, Pavia (IT); Cristina Bonferoni, Pavia (IT); Giuseppina Sandri, Pavia (IT); Luigi Maria Longo, Lainate (IT); Cristina Macelloni, Lainate (IT); Silvia Rossi, Pavia (IT)

(73) Assignee: COSMO TECHNOLOGIES LTD., Dublin (IE)

( * ) Notice: Subject to any disclaimer, the term of this patent is extended or adjusted under 35 U.S.C. 154(b) by 0 days.

(21) Appl. No.: 16/956,872

(22) PCT Filed: Dec. 20, 2018

(86) PCT No.: PCT/EP2018/086424
§ 371 (c)(1),
(2) Date: Jun. 22, 2020

(87) PCT Pub. No.: WO2019/122253
PCT Pub. Date: Jun. 27, 2019

(65) Prior Publication Data
US 2021/0154300 A1 May 27, 2021

(30) Foreign Application Priority Data
Dec. 22, 2017 (EP) ..................................... 17210119

(51) Int. Cl.
| | |
|---|---|
| *A61K 9/08* | (2006.01) |
| *A61K 9/00* | (2006.01) |
| *A61K 9/107* | (2006.01) |
| *A61K 35/33* | (2015.01) |
| *A61K 47/10* | (2017.01) |
| *A61K 47/34* | (2017.01) |
| *A61K 47/36* | (2006.01) |
| *A61K 47/38* | (2006.01) |
| *A61P 17/02* | (2006.01) |

(52) U.S. Cl.
CPC ............ *A61K 47/34* (2013.01); *A61K 9/0019* (2013.01); *A61K 9/08* (2013.01); *A61K 9/1075* (2013.01); *A61K 35/33* (2013.01); *A61K 47/10* (2013.01); *A61K 47/38* (2013.01); *A61P 17/02* (2018.01)

(58) Field of Classification Search
CPC ....... A61K 2300/00; A61K 9/08; A61K 47/38; A61K 9/0053; A61K 47/36; A61K 9/1652; A61K 9/5161; A61K 9/0019; A61K 45/06; A61L 2300/602
See application file for complete search history.

(56) References Cited

U.S. PATENT DOCUMENTS

| | | | | |
|---|---|---|---|---|
| 5,124,151 A | * | 6/1992 | Viegas | .................... A61K 47/36 514/772.7 |
| 5,143,731 A | * | 9/1992 | Viegas | ................. A61K 9/0014 514/967 |
| 5,510,119 A | * | 4/1996 | Santus | ................. A61K 9/0095 424/490 |
| 2003/0108610 A1 | * | 6/2003 | Flore | ...................... A61K 31/77 424/9.1 |
| 2011/0008266 A1 | | 1/2011 | Tamarkin et al. | |
| 2011/0256089 A1 | | 10/2011 | Lim et al. | |
| 2015/0273072 A1 | | 10/2015 | Hsu | |

FOREIGN PATENT DOCUMENTS

| | | | |
|---|---|---|---|
| CN | 101137370 A | 3/2008 | |
| CN | 101827523 A | 9/2010 | |
| EP | 3078367 A1 | 12/2016 | |
| EP | 3173067 A1 | 5/2017 | |
| JP | 2003-504402 A | 2/2003 | |
| JP | 2006-225398 A | 8/2006 | |
| WO | WO-2016161537 A1 * | 10/2016 | ........... A61K 31/439 |
| WO | 2017/017631 A2 | 2/2017 | |

OTHER PUBLICATIONS

LKT Labs. Granisetron Hydrochloride. Date retrieved Jan. 9, 2023. <https://lktlabs.com/product/granisetron-hydrochloride/>. (Year: 2023).*
N Devina et al 2018 J. Phys.: Conf. Ser. 1073 052012 (Year: 2018).*
Office Action in Russian application No. 2020124103 dated Oct. 25, 2021, 2 pages.
The International Search Report and the Written Opinion issued for International application No. PCT/EP2018/086424, dated Mar. 14, 2019, 13 pages.
Giuseppina Sandri et al, An In Situ Gelling Buccal Spray Containing Platelet Lysate for the Treatment of Oral Mucositis, Current Drug Discovery Technolog i es, vol. 8, No. 3, Sep. 2011, pp. 277-285.
Pramod K Kolsure et al, "Development of zolmitriptan gel for nasal administration", Asian Journal of Pharmaceutical and Clinical Research, vol. 5, No. 3, 2012, pp. 88-94.
Dewan Mitali et al. "Effect of gellan gum on the thermogelation property and drug release profile of Poloxamer 407 based ophthalmic formulation", International Journal of Biological Macromolecules, Elsevier BV, NL, vol. 102, Apr. 5, 2017, pp. 258-265.

(Continued)

*Primary Examiner* — Tracy Liu
(74) *Attorney, Agent, or Firm* — Rothwell, Figg, Ernst & Manbeck, P.C.

(57) ABSTRACT

The invention provides a composition for use as a delivery vehicle comprising at least one thermo-responsive polymer (polymer A) and at least one ion-sensitive polymer (polymer B) in a liquid formulation. Polymer A is preferably a polyoxyethylene-polyoxypropylene block copolymer or a cellulose derivative. Polymer B a polysaccharide. The composition can include an active substance for delivery or can be used as a delivery vehicle for a substance added at the time of administration such as mesenchymal stem cells.

11 Claims, 8 Drawing Sheets

(56) References Cited

OTHER PUBLICATIONS

Yuan Yuan et al., "Thermosensitive and mucoadhesive in situ gel based on poloxamer as new carrier for rectal administration of nimesulide", International Journal of Pharmaceutics, Elsevier, NL, vol. 430, No. 1, Mar. 29, 2012, pp. 114-119.
Anna-Lena Kjøniksen et al, "Stabilization of pluronic gels in the presence of different polysaccharides", Journal of Applied Polymer Science, (Jul. 5, 2014), vol. 131, No. 13, Jul. 5, 2014, 8 pages.
Mircea Teodorescu et al., "Novel Thermoreversible Injectable Hydrogel Formulations Based on Sodium Alginate and Poly(N-Isopropylacrylamide)", International Journal of Polymeric Materials., vol. 64, No. 15, Nov. 22, 2015, pp. 763-771.
Bradley A. Borden et al, "Thermoresponsive Hydrogel as a Delivery Scaffold for Transfected Rat Mesenchymal Stem Cells", Molecular Pharmaceutics, vol. 7, No. 4, Aug. 2, 2010, pp. 963-968.
K. Poon et al., "Polymeric hydrophilic polymers in targeted drug delivery", Artificial Cells, Cell Engineering and Therapy, US, CRC Press, (2007), pp. 42-71.
Wenyi Wang et al, "Dual-functional transdermal drug delivery system with controllable drug loading based on thermosensitive poloxamer hydrogel for atopic dermatitis treatment", Scientific Reports, vol. 6, No. 1, Apr. 19, 2016, pp. 1-10.
Ryan F. Donnelly et al, "Chapter 10: Bioadhesive Systems for Drug Delivery", Bioadhesion and Biomimetics: From Nature to Applications, Pan Stanford Publishing, (2015), pp. 235-268.
Examination Report for Indian patent application No. 202017021255 dated Feb. 9, 2022, 7 pages.
Kesavan, K., et al. (2010). "Sodium alginate based mucoadhesive system for gatifloxacin and its in vitro antibacterial activity," Scientia Pharmaceutica, 78(4), 941-957.
Office Action in Japanese Patent Application No. 2020-534389 dated Oct. 11, 2022 (English translation), 4 pages.
Office Action in application No. RU 020124103/04 dated Mar. 24, 2022, with machine English translation, 15 pages.

* cited by examiner (mean values ± s.e.; n=3) (t test p<0.05; a vs b; a' vs b')

(mean values ± s.d.; n=3)

(mean values ± s.d.; n=3)

(mean values ± s.d.; n=3)

(mean values ± s.d.; n=3)

LIQUID DELIVERY COMPOSITION

CROSS REFERENCE TO RELATED APPLICATION(S)

This application is a 35 U.S.C. § 371 National Stage of International Patent Application No. PCT/EP2018/086424, filed Dec. 20, 2018, designating the United States, which claims priority under 35 U.S.C. § 119 to European Patent Application No. 17210119.8, filed Dec. 22, 2017, the disclosures of which are incorporated by reference in their entirety.

The present invention provides an innovative combination of biomaterials formulated in a liquid composition for use as a versatile delivery vehicle in many pharmaceutical and non-pharmaceutical fields. The liquid composition comprising the combination of biomaterials of the invention is provided as a delivery vehicle for medical purposes in humans.

BACKGROUND OF THE INVENTION

Biomaterials are substances that interact with biological systems for a medical purpose—either a therapeutic (treat, augment, repair or replace a tissue function of the body), a protective or a diagnostic one.

Biomaterials can be derived either from nature or synthesized in the laboratory using a variety of chemical approaches.

Biocompatibility is related to the behavior of biomaterials in various environments under various chemical and physical conditions. The term may refer to specific properties of a material without specifying where or how the material is to be used. For example, a material may or may not able to integrate with a particular cell type or tissue. The ambiguity of the term reflects the ongoing development of insights into if and how biomaterials interact with the human body and eventually how those interactions determine the clinical success of a medical device or a drug.

Control of the delivery of active substances in the human body is important for medical purposes. In the case of specific targets, site-specificity of the delivery may be crucial to obtain the desired medical result. In the case of other specific targets, site-specificity of delivery and the time of action represent the only way to obtain a successful result and can represent an important aspect of the compliance for the subject or for the patient. In addition, in many therapeutic applications, there is the need to obtain a prolonged, sustained release of the active substance for the achievement of a prolonged contact with the application site, where. it is important to maintain the concentration of the active substance above the Minimum Effective Concentration (MEC) for a prolonged time; the first outcome of this property is a consequent decrease in the frequency of administrations, which translates into increased patient compliance, ensuring a higher possibility for the patients to achieve symptoms remission or disease healing.

There is a need to provide innovation in the field of the delivery of active substances, following the progresses of chemistry and physics of the biomaterials especially for in-situ delivery vehicles that are able to provide a prolonged residence time for the active substances.

There is also a need for a delivery vehicle for use in a well-defined selective location or clinical setting where an active substance can be added to the delivery vehicle and administered to a patient for immediate delivery to a target site.

DISCLOSURE OF THE INVENTION

The present invention provides a composition for use as a delivery vehicle comprising at least one thermo-responsive polymer (polymer A) and at least one ion-sensitive polymer (polymer B) in a liquid formulation.

Preferably polymer A is chosen from the group comprising but not limited to: polyoxyethylene-polyoxypropylene block copolymers, such as poloxamer 124, poloxamer 188, poloxamer 237, poloxamer 338, poloxamer 407 and the like, poly(ethylene glycol)/poly(lactide-coglicolide) block copolymers (PEG-PLGA), poly(ethylene glycol)-poly(lactic acid)-poly(ethylene glycol) (PEG-PLA-PEG), poly(N-isopropylacrylamide), and cellulose derivatives, like methylcellulose (MC) and hydroxypropylmethylcellulose (HPMC) and the like and mixtures thereof.

Preferably polymer B is chosen from the group comprising but not limited to: carrageenan, gellan gum, pectin, alginate and the like and mixtures thereof.

The liquid composition of the invention herein disclosed may further comprise at least one bio-adhesive polymer (polymer C) selected from the group comprising, but not limited to: chitosan, hyaluronic acid and salts thereof, cellulose derivatives, such methyl cellulose, hydroxy propyl methylcellulose, hydroxy propyl cellulose, carboxymethyl cellulose sodium and the like, polyvinyl alcohol, polyvinyl pyrrolidone, polyacrylic acid, poly ethylene oxides, cyclodextrins, tragacanth, sodium alginate, xanthan gum, gelatin, pectin, and the like and mixtures thereof.

The composition may further comprise at least one other excipient such as antioxidants, chelating agents, preservatives and/or antimicrobial agents, surfactants, co-surfactants, lipophilic compounds, purified water or water for injection, organic and inorganic salts, buffers agents having trophic activity.

In one embodiment the composition further comprises at least one active substance for delivery.

The at least one active substance can be selected from the group comprising proteins or peptides, monoclonal antibodies, cytokines, anti-acids, adrenergic drugs, anti-adrenergic drugs, dyes, immune-stimulants, steroidal and non-steroidal anti-inflammatory drugs, antihistamines, nasal antihistamines/decogestionants, anti-diarrheals, antineoplastics, antimicrobics, antibiotics, antifungal drugs, antihemorroidal drugs, anti-adrenergic drugs, adrenergic drugs, analgesics, bronchodilators, selective alpha-2 antagonists, anticholinergics/antispasmodics, peripheral opioid receptors antagonists, laxatives, genitourinary tract agents, cathartics, vaginal agents, vaginal antifungal, vaginal antibiotics, oral cavity disinfectants or oral cavity antibiotics, wound healing drugs, haemostatics, anaesthetics, sclerosant drugs, or a mixture thereof.

In yet another embodiment the composition is formulated such that an active substance can be added at the time of administration, especially extemporaneously.

The active substance added at the time of administration can be any or the above and can also be a cellular material, including cells and or cell components such as for example microvescicles, genomic material and lysosomes.

The cells can be differentiated cells derived from ectoderm, comprising but not limited to skin cells and melonocytes; endoderm, comprising but not limited to alveolar cells and pancreatic cells; and mesoderm, comprising but not limited to cardiac muscle cells and skeletal muscle cells; or stem cells such as embryonic stem cells, tissue-specific stem cells, mesenchymal stem cells and induced pluripotent stem cells, preferably mesenchymal stem cells (MSCs).

The invention provides a composition as described herein for use in the delivery of the cellular material as above disclosed. The invention provides a composition as described herein for use in the delivery of cells preferably stem cells, more preferably mesenchymal stem cells. The cells can be added to the vehicle composition at the time of administration.

In order to save the functionality and the living properties the cells should be added within a period not exceeding eight hours prior to administration and preferably not exceeding six hours.

According to one aspect of the invention, the liquid composition is for use as a delivery vehicle in humans.

According to another aspect of the invention, the liquid composition is for use in the diagnosis, prevention, alleviation, treatment and/or reduction of pathologies or disorders affecting the human body.

A non-limiting and detailed description of the invention follows with reference to non-limiting examples and figures.

BRIEF DESCRIPTION OF THE DRAWINGS

The drawings directly relate to the Examples set out herein and are explained in detail later in this document.

DETAILED DESCRIPTION OF THE INVENTION

Figure 1:
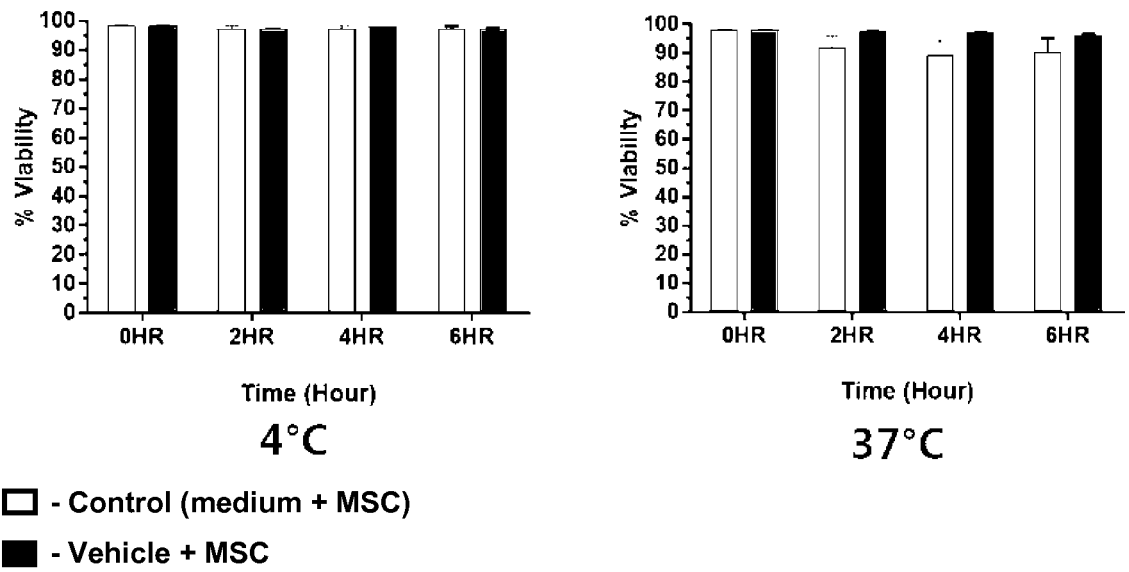
FIG. 1 reports the viability of MSC after 2, 4 and 6 hours of contact with MSC suspension vehicle at 4° C. and 37° C. Clear bars: Control (medium+MSC); Solid Bars: Vehicle+MSC.

It has been surprisingly found that the combination of certain biomaterials leads to obtain a new delivery vehicle, able to target at least one active substance to the specific site of action and able to maintain the substance at the site for a prolonged time.

The combination of biomaterials of the invention comprises at least one thermo-responsive polymer (polymer A) and at least one ion-sensitive polymer (polymer B) in a composition, preferably in a liquid form.

The combination of biomaterials of the invention may further comprise at least one bio-adhesive polymer (polymer C).

In some embodiments, the combination of biomaterials of the invention is preferably formulated in a liquid composition, together with at least one active agent and at least one physiologically acceptable excipient.

In other embodiments, the combination of biomaterials of the invention is preferably formulated in a structured viscous composition, together with at least one active agent and at least one physiologically acceptable excipient. According to these embodiments, the structured viscous composition is similar to a semisolid vehicle and/or to a soft gel, retaining a certain degree of mobility of a liquid and can further structure itself and gelifies upon contact with a biorelevant medium at the site of action.

One object of the invention is a combination of at least one thermo-responsive polymer (polymer A) and at least one ion-sensitive polymer (polymer B) as below disclosed.

Another object of the invention is a combination of at least one thermo-responsive polymer (polymer A) and at least one ion-sensitive polymer (polymer B), further containing at least one bio-adhesive polymer (polymer C).

Another object of the invention is a liquid composition comprising a combination of at least one thermo-responsive polymer (polymer A) and at least one ion-sensitive polymer (polymer B), at least one active substance and at least one physiologically acceptable excipient as below disclosed.

Another object of the invention is a liquid composition comprising a combination of at least one thermo-responsive polymer (polymer A), at least one ion-sensitive polymer (polymer B), at least one bio-adhesive polymer (polymer C), at least one active substance and at least one physiologically acceptable excipient as below disclosed.

Another object of the invention is a structured viscous composition comprising a combination of at least one thermo-responsive polymer (polymer A) and at least one ion-sensitive polymer (polymer B), as below disclosed.

Another object of the invention is a structured viscous composition comprising a combination of at least one active substance and at least one physiologically acceptable excipient as below disclosed.

Another object of the invention is a structured viscous composition comprising a combination of at least one thermo-responsive polymer (polymer A), at least one ion-sensitive polymer (polymer B), at least one bio-adhesive polymer (polymer C), at least one active substance and at least one physiologically acceptable excipient as below disclosed.

The liquid composition of the invention can be a solution, a micellar dispersion, a suspension, an emulsion or a micro-emulsion. Solutions and suspensions of the invention are water-based solution or water-based suspensions. Emulsions or micro-emulsions of the invention are oil-in-water or water-in-oil emulsions or micro-emulsions. The liquid composition of the invention can be a structured viscous composition or a soft gel.

The liquid composition of the invention can be administered by oral, buccal, dental, ocular, rectal, perianal, vaginal, ear or nasal route or by injection. The composition of the invention can be also administered topically, preferably by direct application or by injection.

The liquid composition of the invention can be administered directly to cavities created surgically, from disease or resulting from injury.

The liquid composition comprising the combination of biomaterials of the invention can be then also administered by injection, by, sub-mucosal, intraperitoneal, intra-tumoral, sub-cutaneous, intramuscular, intraarticular, intranasal, intrathecal, epidural, intra-parenchymal to the brain or spinal cord or to sub-retinal spaces. The liquid composition of the invention can be in sterile or non-sterile form.

The liquid composition of the invention can be in form of enema, syrup, drop, solution, suspension, micellar dispersion, emulsion, micro-emulsion, structured viscous vehicle, viscous vehicle structured in a soft gel, vaginal douche, irrigation composition, liquid composition in soft gel capsules.

The liquid composition of the invention can be used as a versatile delivery vehicle in many pharmaceutical and non-pharmaceutical fields. The liquid composition of the invention is provided as a delivery vehicle for pharmaceutical and/or medical purposes in humans.

The liquid composition comprising the combination of biomaterials of the invention can be used to deliver the at least one active substance directly in the gastro-intestinal tract, in the bladder, in the vagina, in the eyes, in the ears, in the nose and any other tissue or organ in which it could be useful by direct application or by injection.

Another object of the invention is the liquid composition comprising the combination of combination of at least one thermoresponsive polymer (polymer A) and at least one ion-sensitive polymer (polymer B) for use as delivery vehicle as below disclosed.

Another object of the invention is the liquid composition comprising the combination of at least one thermo-responsive polymer (polymer A) and at least one ion-sensitive polymer (polymer B) for use as delivery vehicle for pharmaceutical or medical purposes in humans as below disclosed.

Another object of the invention is the liquid composition comprising the combination of at least one thermo-responsive polymer (polymer A) and at least one ion-sensitive polymer (polymer B) for use in the diagnosis, prevention, alleviation, treatment and/or reduction of pathologies or disorders affecting the human body as below disclosed.

Another object of the invention is the structured viscous composition comprising the combination of at least one thermo-responsive polymer (polymer A) and at least one ion-sensitive polymer (polymer B) for use as delivery vehicle as below disclosed.

Another object of the invention is the structured viscous composition comprising the combination of at least one thermo-responsive polymer (polymer A) and at least one ion-sensitive polymer (polymer B) for use as delivery vehicle for pharmaceutical or medical purposes in humans as below disclosed.

Another object of the invention is the structured viscous composition comprising the combination of at least one thermo-responsive polymer (polymer A) and at least one ion-sensitive polymer (polymer B) for use in the diagnosis, prevention, alleviation, treatment and/or reduction of pathologies or disorders affecting the human body as below disclosed.

Thanks to the combination of at least one thermo-responsive polymer (polymer A) and at least one ion-sensitive polymer (polymer B) it is possible to maintain the vehicle grafted to the target organ or to the mucosa and to modulate the release in situ of the at least one active substance from the liquid or structured viscous composition of the invention according to a desired profile, at a desired site of action and with a desired time of permanence of the active substance at the site of action.

In fact, the unexpected synergic effect on the structuring and bio-adhesive properties has been found where the two types of biomaterials are included in the same composition: the combination of said at least one thermo-responsive polymer (polymer A) and at least one ion-sensitive polymer (polymer B) produces an unexpected increase of their ability to interact with the human body, in tissues or organs. Both types of polymers are independently able to gelify or to structure themselves upon contact with a bio-relevant medium as, for instance, the extracellular matrix of a mucosa; it has been now surprisingly discovered that, when combined together, polymer A synergistically strengthen the interaction with the bio-relevant medium of the polymer B or vice-versa, resulting in an expansion of their capability to gelify or to structure. The combination therefore, interacting with the system rheology, modulates the release of the at least one active substance from the liquid composition of the invention at the desired site, enhancing the permanence and the residence time at the site.

The mechanisms of action of these biomaterials are different: the thermo-responsive polymer (polymer A) when the temperature reaches a suitable range of values gelifys to create a structure with the bio-relevant medium and the ion-sensitive polymer (polymer B) gelifys to create a structure with the bio-relevant medium in the presence of specific ions in suitable concentrations.

In one embodiment, the first polymer (A) after contact with the bio-relevant medium gelifys or creates a structured composition at physiological temperature (i.e. at about 37° C.) and in parallel allows the interaction of the polymer B with the site of action, where the presence of a specific starter ion strengthening the interaction with the environmental medium of the other, resulting in an expansion of the mixture capability of gelifying or structuring. The combination of the invention works thanks to an optimal combination of the two polymers A and B that lead to a strong synergism between the polymers themselves and the polymers with the microenvironment, leading to a strengthened gelation/structuring of the composition at the site of action.

Such strengthened gelation is demonstrated by a huge increase in the viscoelastic modulus G'. The transition from a liquid form to a gel state or to a structured composition state, enhances the composition's bio-adhesiveness, with a subsequent enhancement of the adhesion properties at the administration site for a suitable period of time, as demonstrated by the differential parameter $\Delta G'$, calculated as the difference between G' values observed at physiological temperature (i.e. about 37° C.) and at room temperature (i.e. about 25° C.) of the composition. It has been surprisingly discovered that the differential parameter $\Delta G'$ remains unaltered upon dilution with water and/or with a bio-relevant medium (such as, for example the Simulated Colonic Fluid or in Artificial Saliva). Such strengthened gelation or structuring is also responsible for a higher permanence of the liquid composition at the administration/application site prolonging the residence time of the active substance. This allows to have a versatile liquid vehicle composition able to target at least one active substance at a desired site of action (in situ) for a desired time of permanence. This unexpected flexibility allows the liquid composition to be used as a vehicle for many application, in pharmaceutical and non-pharmaceutical fields.

The combination of polymer A and polymer B provides the composition of the invention with bio-adhesive properties which allow the composition to adhere and/or to bind to the target tissue or to the target organ, such as the mucosa and/or the submucosa, for a suitable period of time.

The composition of the invention therefore is a flexible vehicle that, thanks to the increased grafting properties to selected tissues or organs, is able to control the release of an active substance in view of the desired site of action and in view of the desired duration of such action.

A similar vehicle advantageously allows a control of the release profile of active substance/s depending on the different diseases to be treated that requires this kind of improved properties. A structured vehicle has more capacity of control the mobility of disperse active substances or creates more resistance to the diffusion of active substances solubilized from the internal side of the depot to the The composition of the invention can act as a reservoir or as depot.

According to the invention herein disclosed, the composition contains at least one thermo-responsive polymer (polymer A) and one ion sensitive polymer (polymer B).

In the preparation of liquid compositions according to the invention herein disclosed, the choice of the suitable thermo-responsive polymers (polymer A) and of their concentration may be made to obtain a final composition which is in liquid state below the body temperature (i.e. below about 37° C., preferably at about 20-25° C.) and which becomes a gel or a structured composition once exposed to the body temperature or above (i.e. at or above about 37° C.).

In the preparation of liquid compositions according to the invention herein disclosed, the choice of the suitable ion-sensitive polymer (polymer B) and of their concentration may be made to obtain a suitable sol-gel transition or a transition to a structured composition in presence of specific ions.

According to the invention, an ion-sensitive polymer can be selected among those able to bind mono and/or divalent inorganic ions, such as $Na^+$, $K^+$, $Mg^{2+}$, $Ca^{2+}$ and $Zn^{2+}$, and organic ionswith high affinity. The responsiveness to ionic strength is a typical property of polymers containing ionizable groups. Changes in ionic strength may cause changes in the size of the polymeric micelles and polymer solubility.

When administered, due to the superior flowability properties of the liquid composition according to the invention herein disclosed, said composition is automatically heated to body temperature (i.e. about 37° C.), thus transitioning from liquid to a gel state (sol-gel transition) or to a structured state due to the thermos-responsive polymer A; then, through the interaction of the ion sensitive polymer B with the ions present in the biorelevant medium and/or environment, said gel or structured composition is further strengthened, as demonstrated by a huge increase in the viscoelastic modulus G'.

In order to better point out the synergic interaction between the two polymers, it is observed an improvement of the strength of a gel based on one at least thermos-responsive polymer, in the physiological range of temperature (ie. about 37° C.), with the combination of Polymer A and Polymer B. Such an improvement is indicated by ΔG' values, higher for the combination of the two polymers with respect to a solution of a thermo-responsive polymer alone, a further improvement is obtained upon dilution with biorelevant medium.

The transition from a liquid form to a gel state or a structured state, according to such aspects of the invention, enhances the composition bio-adhesiveness, with a subsequent enhancement of their adhesion to the tissues, such as the mucosa and/or the submucosa, at the administration site for a suitable period of time as demonstrated by the differential parameter ΔG', calculated as the difference between G' values observed at physiological temperature (i.e. about 37° C.) and at room temperature (I.e. about 25° C.) of the composition as is and upon dilution with biorelevant medium (Simulated Colonic Fluid or in Artificial Saliva).

Moreover, the increase of the viscoelastic modulus of the pharmaceutical liquid compositions of the invention slows down the diffusion of the at least one active substance, delaying its delivery to the affected site, with prolongation of the therapeutic effect. When administered by injection into the body, the composition of the invention is automatically heated to body temperature (i.e. about 37° C.), thus transitioning from liquid to gel form with a huge increase of its viscosity, thanks to the presence of the thermo-responsive polymer; then, the interaction of the ion-sensitive polymer with the ions at the site of injection further strengthens the gel or the structured composition. This results in the formation of a depot at the site of injection with a slow release profile of the at least one active substance.

When administered the liquid compositions according to such aspects of the invention are able to form a thin gel or structured layer over the affected area, having a reduced tendency to flow along the organ walls. This maximizes the contact time between said liquid compositions according to such aspects of the invention, and the affected area: as a result, said at least one active agent contained therein remains in contact with the cell membrane of the epithelial cells of the mucosa for a longer period of time, in comparison with known composition.

According to the invention herein disclosed, said at least one thermo-responsive polymer (polymer A) may be selected in the group comprising, but not limited to: poly-oxyethylene-polyoxypropylene block copolymers, such as poloxamer 124, poloxamer 188, poloxamer 237, poloxamer 338, poloxamer 407 and the like, poly(ethylene glycol)/poly(lactide-coglicolide) block copolymers (PEG-PLGA), poly(ethylene glycol)-poly(lactic acid)-poly(ethylene glycol) (PEG-PLA-PEG), poly(N-isopropylacrylamide), and mixtures thereof.

Any mixture of the above thermo-responsive polymers can be used to form the appropriate liquid composition.

Among the thermo-responsive polymers some cellulose derivatives, like methylcellulose (MC), hydroxypropylmethylcellulose (HPMC) and methyl (hydroxyethyl) cellulose may also be selected.

In a preferred aspect, the thermo-responsive polymer of said liquid composition is poloxamer 188.

In another preferred aspect, the thermo-responsive polymer of said liquid composition is poloxamer 407.

Further in another preferred aspect, said thermo-responsive polymer comprises some mixtures of poloxamer 188 and poloxamer 407.

In another preferred aspect, the thermo-responsive polymer of said liquid composition is methylcellulose.

According to the invention herein disclosed, the amount of said at least one thermo-responsive polymer ranges between about 0.1% to about 30% by weight with respect to the weight of the liquid composition, more preferably between about 0.2% to about 25% by weight with respect to the weight of the liquid composition, much more preferably between about 0.3% and about 25% by weight with respect to the weight of the liquid composition.

According to a preferred aspect, said at least one thermo-responsive polymer is contained in an amount of about 0.1% or about 0.3% or about 1.0% or about 5.0% or about 10.0% or about 15% or about 20% or about 25% or about 30% by weight with respect to the weight of the liquid composition.

According to the invention herein disclosed, said at least one ion sensitive polymer (Polymer B) may be selected in the group of polysaccharides, comprising, but not limited to carrageenan, gellan gum, pectin, alginic acid and/or salts thereof. Said at least one ion-sensitive polymer, may be, for example sodium alginate.

According to the invention herein disclosed, said at least one ion-sensitive polymer is contained in an amount which ranges from about 0.001% to about 10% by weight with respect to the weight of the composition, preferably from about 0.005% to about 5% by weight with respect to the weight of the composition, more preferably from about 0.01% to about 2.0% by weight with respect to the weight of the composition.

According to a preferred aspect, said at least one ion-sensitive polymer is contained in an amount of about 0.1% or about 0.2% or about 0.3% or about 0.5% or about 1% or about 2% by weight with respect to the weight of the liquid composition.

According to the invention herein disclosed, the liquid composition may further comprise at least one surfactant; according to one aspect, the at least one surfactant may be selected in the group of the non-ionic surfactants, comprising, but not limited to: PEG-fatty acid monoesters surfactants, such as PEG-15 hydroxystearate, PEG-30 stearate, PEG-100 monostearate (also known as polyoxyl 100 monostearate), PEG-40 laurate, PEG-40 oleate and the like; PEG-fatty acid diesters surfactants, such as PEG-32 dioleate, PEG-400 dioleate and the like; polyoxyethylene sorbitan fatty acid esters, such as polysorbate 20, polysorbate 60, polysorbate 80 and the like; polyoxyethylene alkyl ethers, such as PEG-20 cetostearyl ether, polyoxyl 25 cetostearyl, cetomacrogol 1000 and the like; sorbitan fatty acid esters surfactants, such as sorbitan monolaurate, sorbitan monopalmitate, sorbitan monooleate, sorbitan monostearate and the like; propylene glycol esters of fatty acids; polyglycerol esters of fatty acids; polyoxyethylene castor oil derivatives such as polyoxyl 5 castor oil, polyoxyl 15 castor oil, polyoxyl 35 castor oil, polyoxyl 40 hydrogenated castor oil and the like; caprylocapryl polyoxyil-8 glicerides; polyoxylglycerides such as caprylocaproyl polyoxylglycerides, lauroyl polyoxylglycerides, oleoyl polyoxylglycerides and the like ceteareth 16, ceteareth 20, stearaeth 10, steareth 20, ceteth 20 and the like.

Any mixture of the above non-ionic surfactant can be used to form the appropriate pharmaceutical liquid composition. In one aspect, the non-ionic surfactant is polysorbate 80.

In another aspect, the non-ionic surfactant is sorbitan monostearate. In another aspect, the non-ionic surfactant is polyoxyl 100 monostearate.

In another aspect, the non-ionic surfactant is polyoxyl-35 castor oil. In a preferred aspect, the non-ionic surfactant is PEG-15 hydroxystearate (also known as polyoxyl-15-hydroxystearate).

In another aspect said at least one surfactant may be selected in the group of the ionic surfactants, comprising, but not limited to: egg lecithin, phosphatidyl choline, hydrogenated phosphatidyl choline from egg lecithin, soybean lecithin, hydrogenated soybean lecithin, glycerophosphocholine, soybean lysolecithin, phospholipids, hydrogenated phospholipids, sodium lauryl sulphate and the like.

Any mixture of the above ionic surfactant can be used to form the appropriate pharmaceutical liquid composition. Suitable ionic surfactants are commercialized by Lipoid®, under the brand-name of Lipoid®.

In one aspect, the ionic surfactant is egg lecithin. In another aspect, the ionic surfactant is hydrogenated phosphatidyl choline from egg lecithin. In another aspect, the ionic surfactant is phosphatidyl choline.

In another aspect, the ionic surfactant is soybean lecithin.

Further in another aspect, the ionic surfactant is hydrogenated soybean lecithin.

According to the invention herein disclosed, said at least one surfactant is contained in an amount which ranges from about 0.001% to about 15% by weight with respect to the weight of the liquid composition, preferably from about 0.005% to about 10% by weight with respect to the weight of the liquid composition, more preferably from about 0.01% to about 5% by weight with respect to the weight of the liquid composition.

According to a preferred aspect, said at least one surfactant is contained in an amount of about 0.3% or about 0.5% or about 1% or about 2% or about 3% or about 4% by weight with respect to the weight of the liquid composition.

The composition of the invention herein disclosed may further comprise at least one bio-adhesive polymer selected from the group comprising, but not limited to: chitosan, hyaluronic acid and salts thereof, cellulose derivatives, such methyl cellulose, hydroxy propyl methylcellulose, hydroxy propyl cellulose, carboxymethyl cellulose sodium and the like, polyvinyl alcohol, polyvinyl pyrrolidone, polyacrylic acid, poly ethylene oxides, tragacanth, sodium alginate, xanthan gum, gelatin, pectin, and the like.

Any mixture of the above bio-adhesive polymer may be used to obtain suitable pharmaceutical liquid compositions according to the invention.

In one aspect, said at least one bio-adhesive polymer is chitosan.

In another aspect, said at least one bio-adhesive polymer is sodium alginate.

In a preferred aspect, said at least one bio-adhesive polymer is carboxymethyl cellulose sodium. In another preferred aspect, said at least one bio-adhesive polymer is hyaluronic acid and/or a salt thereof.

According to this aspect, said at least one bio-adhesive polymer provides an additional synergy with the others leading to an improved level of adhesion of the liquid vehicle and an improved residence time at the desired site. In a ideal mechanism of action, the bio-adhesive polymer enhances the grafting possibility to the body tissue for the vehicle whereas the other polymers enhance the structure of the gelling layer obtained by spreading the vehicle composition of the invention on the target body surface to act as a reservoir or as a depot or in any case ensuring the persistence and the effect.

According to this aspect, the efficacy of the active substance contained in the liquid delivery vehicle can be maximized According to the invention, said at least one physiologically acceptable excipients can include an aqueous phase having hydrophilic characteristics and, if needed, an oily phase having lipophilic characteristics.

Thus, said liquid composition can solubilize both hydrophobic (lipophilic) and hydrophilic active substances. In case of hydrophobic (lipophilic) active substances, the oily phase can be varied, in composition and quantity, to achieve a complete solubilization of said hydrophobic (lipophilic) substance into said oily phase. In case of hydrophilic active substances, the aqueous phase can be varied, in quantity, to achieve a complete solubilization of said hydrophilic active substance into said aqueous phase. Due to the presence of a water-based solvent in case of hydrophilic active substance, or two phases of different polarity, hydrophobic (lipophilic) and hydrophilic active substances, in case of hydrophobic active substances, both hydrophilic and hydrophobic active substance can be formulated into the same pharmaceutical liquid composition in form of micellar dispersion, emulsion, microemulsion or water based solution of the invention Due to all these favorable features, the liquid composition of the invention can solubilize active substances having different polarities.

In some aspect, the liquid composition of the invention comprises at least one hydrophobic active substance.

In other aspects, the I liquid composition of the invention comprises at least one hydrophilic active substance.

In other aspects, the pharmaceutical liquid composition of the invention comprises at least one hydrophobic active substance and at least one hydrophilic active substance.

The control of the release is achieved by a long-lasting diffusion—thanks to the contribution of the bio-adhesive forces—of the active substance from the liquid composition of the present invention into the tissue and/or into the sub-mucosal/mucosal layer of gastrointestinal tract Moreover, the increase of the viscoelastic modulus of the liquid compositions of the invention slows down the diffusion of the at least one active substance, delaying its delivery to the affected site, with prolongation of the therapeutic effect.

Thus, for the pharmaceutical liquid compositions according to such aspects of the invention, the reversible thermo-responsive sol-gel transition, in response to contact with the target site, combined with the expansion of the mixture capability of gelifying thanks to the presence of the polymer B, act efficaciously in determining the release profile of the at least one active substance, which can act on the affected site for a prolonged time When administered by injection the liquid composition of the invention creates a depot of said at least one active substance, ensuring a reservoir of the same leading to constant release, improved local bioavailability (at the administration site) and prolonged efficacy: the control of the release is achieved by a slow erosion of the depot, with a long-lasting diffusion of said at least one active substance into the tissue and/or into the sub-mucosal/mucosal layer.

This allows the effective administration of the optimal dose of active substance even with a single session of injection or with a reduced number of injection's session, avoiding or reducing the need for repeated sessions of injections over time.

When administered by oral, vaginal or rectal route, the liquid composition of the invention forms a thin gel layer over the affected area, having a reduced tendency to flow along the organ walls. This maximizes the contact time between said liquid compositions and the affected area: as a result, said at least one active substance contained therein remains in contact with the cell membrane of the epithelial cells of the mucosa for a longer period of time, in comparison to a simple pharmaceutical liquid composition.

The invention herein disclosed refers to a liquid composition and the same for use as a delivery vehicle in humans wherein said pharmaceutical liquid composition comprises:

(a) at least one thermo-responsive polymer (polymer A)
(b) at least one ion sensitive polymer (polymer B);
(c) optionally at least one physiologically acceptable excipient.

The invention herein disclosed refers to a liquid composition and the same for use as a delivery vehicle in humans wherein said pharmaceutical liquid composition comprises:

(a) at least one thermo-responsive polymer (polymer A)
(b) at least one ion sensitive polymer (polymer B);
(c) at least one active substance;
(d) optionally at least one physiologically acceptable excipient.

According to the invention, said at least one active substance can be selected from the group comprising proteins or peptides, monoclonal antibodies, cytokines, anti-acids, adrenergic drugs, anti-adrenergic drugs, dyes, immune-stimulants, steroidal and non-steroidal anti-inflammatory drugs, antihistamines, nasal antihistamines/decogestionant agents, anti-diarrheals, antineoplastics, antimicrobics, antibiotics, antifungal drugs, antihemorroidal drugs, anti-adrenergic drugs, adrenergic drugs, analgesics, bronchodilators, selective alpha-2 antagonists, anticholinergics/antispasmodics, peripheral opioid receptors antagonists, laxatives, genitourinary tract agents, cathartics, vaginal agents, vaginal antifungal, vaginal antibiotics, oral cavity disinfectants or oral cavity antibiotics, wound healing drugs, haemostatics, anaesthetics, sclerosant drugs, or a mixture thereof.

Suitable anti-acids can be selected from citric acid, sodium citrate, sodium bicarbonate, magnesium carbonate, magnesium oxide or mixtures thereof. According to one preferred aspect, the citric acid is citric acid monohydrate.

According to one preferred aspect, the sodium citrate is sodium citrate dihydrate.

Suitable dyes can be selected from vital dyes (or absorptive dyes), non-vital dyes (or contrast dyes), and reactive dyes.

According to the invention herein disclosed, said vital (or absorptive) dye may be selected in the group comprising, but not limited to: Lugol's solution, methylene blue, toluidine blue, crystal violet and the like.

According to the invention herein disclosed, said non-vital (or contrast) dye may be selected in the group comprising, but not limited to: indigo carmine and the like. According to the invention herein disclosed, said reactive dye may be selected in the group comprising, but not limited to: congo red, phenol red and the like. Any mixture of the above dyes can be used to form the appropriate liquid composition.

According to a preferred embodiment, said at least one dye is methylene blue.

According to another preferred embodiment, said at least one dye is indigo carmine.

Suitable immune-stimulants according to the present invention are selected from *Saccharomyces cerevisiae*, arginine, resveratrol, *Astragalus membranaceus, echinacea uncaria*, interferons, interleukins, colony stimulating factors, and mixtures thereof.

Suitable antimicrobics or antibiotics according to the present invention are selected from rifamycin SV, rifaximin, rifampicin, tetracyclines, benzalkonium bromide, aminoglycosides, cephalosporins, penicillins, macrolides, ansamycines, sulphonamides, carbapenemes or mixtures thereof. Suitable topical antimicrobials according to the present invention are selected from zinc oxide, silver or salt thereof, silver sulfadiazine, silver oxide, iodine, chlorhexidine, povidone iodide and mixtures thereof.

Suitable haemostatic drugs can be selected from epinephrine, norepinephrine, mixture and/or salts thereof.

Suitable sclerosant drugs can be selected from ethanolamine oleate, sodium morrhuate 5%, sodium tetradecyl sulfate 1% and 3%, polidocanol 0.5%-3%, absolute alcohol, hypertonic (50%) dextrose solution, mixture and/or salts thereof.

Suitable anaesthetic drugs can be selected from lidocaine, bupivacaine, mepivacaine, articaina, benzocaine, tetracaine, prilocaine, mixture and/or salts thereof.

Suitable anti-inflammatory drugs are selected from steroidal anti-inflammatory drugs, non-steroidal anti-inflammatory drugs, or mixtures thereof.

Steroidal anti-inflammatory drugs according to the present invention are selected from cortisone, hydrocortisone, prednisone, prednisolone, methylprednisolone, budesonide, triamcinolone, acetonide, betamethasone, beclometasone, triamcinolone, dexamethasone, mometasone, desonide, fluocinolone, esters, salts thereof or a mixture thereof.

Non-steroidal anti-inflammatory drugs according to the invention are selected from 5-ASA, ketorolac, indomethacin, piroxicam, ketoprofen, naproxen, ibuprofen, diclofenac, difunisal, flurbiprofen, thiaprophenic acid, metamizol, nimesulide, salts thereof or a mixture thereof.

According to a preferred aspect, the active substance is a steroidal anti-inflammatory drug, more preferably budesonide.

Suitable anti-fungal drugs according to the invention are selected from itraconazolo, fluconazole, capsofungin, griseofulvin or a mixture thereof.

Suitable anti-hemorroidals drugs according to the invention are selected from sincatechins, *Saccharomyces cerevisiae*, hydrocortisone, pramoxine, phenlephione or a mixture thereof.

Suitable anti-adrenergic drugs according to the invention are selected from doxazosin, prazosin, terazosin or mixtures thereof.

Suitable adrenergic drugs and beta-adrenergic blocking drugs according to the invention are selected from epinephrine, norepinephrine, salts thereof or mixtures thereof and propranol, sotalol, metoprolol and mixtures thereof.

Suitable analgesics according to the invention are selected from acetaminophen, phenacen, sodium acylate or mixtures thereof.

Suitable bronchodilators according to the invention are selected from albuterol, procaterol, levabuterol and mixtures thereof.

Suitable selective alpha2 antagonists according to the invention are selected from salbutamol, terbutaline, ephedrine, orciprenaline sulfate and mixtures thereof.

Suitable anti-diarrheals according to the invention are selected from loperamide, *Saccharomyces boulardii, Lactobacillus acidophilus, lactobacillus bulgaricus* and mixtures thereof.

Suitable intestinal anti-inflammatories according to the invention are selected from 5-aminosalicylic, olsalazine, sulfasalazine, budenoside and mixtures thereof.

Suitable anticholinergics/antispasmodics according to the invention are selected from octylonium bromide, hyscyamine, atropine, scopolamine, oxybutyin and t mixtures thereof.

Suitable peripheral opioid receptor antagonists according to the invention are selected form smethylnaltrexone, naloxegol and mixtures thereof.

Suitable laxatives according to the invention are selected from magnesium salts (citrate, sulfate, phosphate bicarbonate and the like), *senna*, bisacodyl, lactulose, polyethylene glycols (PEGs), phosphate salts, docusate and mixtures thereof.

Suitable genitourinary tract agents according to the invention are selected from acetohydroxamic acid, phenazopyridine, bethanecol and mixtures thereof.

Suitable nasal antihistamines and decongestants according to the invention are selected from phenylephrine, oxymetazoline, ephedrine, pseudoephedrine, salts thereof and mixtures thereof.

Suitable cathartics according to the invention are selected from bisacodil, sodium picosulfate, PEGs, and mixtures thereof.

Suitable vaginal agents according to the invention are selected from estradiol, estrogens, conjugated estrogens, other hormones and mixtures thereof.

Suitable vaginal antifungals and antibiotics according to the invention clotrimazole, clindamycin, miconazole, metronidazole and mixtures thereof;

Suitable oral cavity disinfectants or antimicrobials according to the invention are selected from benzalkonium chloride, cetylpyridinium chloride or tibezonium iodide, and some amino derivatives such as benzylamine and chlorhexidine as well as the salts and derivatives thereof.

According to a preferred aspect of the invention, the suitable active substance is selected from anti-acids, dyes, immune-stimulants, steroidal and non-steroidal anti-inflammatory drugs, antimicrobics, antibiotics, anti-hemorroidal drugs or a mixture thereof.

The dosage of the least one active substance is designed depending on the diagnosis, prevention, alleviation, treatment and/or reduction of which pathologies or disorders affecting the human body is discussed.

According to one aspect of the invention, the liquid composition is for use as a delivery vehicle in humans.

According to another aspect of the invention, the liquid composition is for use in the diagnosis, prevention, alleviation, treatment and/or reduction of pathologies or disorders affecting the human body.

According to another aspect, the liquid composition of the invention is for use as a delivery vehicle in the gastro-intestinal tract, in the vagina, in the bladder, in the nose, on the ear or in the eye According to another aspect, the liquid composition of the invention is for use in the diagnosis, prevention, alleviation, treatment and/or reduction of pathologies or disorders affecting the gastro-intestinal tract, in the vagina, in the bladder, in the nose and in the eyes.

According to these aspects, the gastrointestinal tract refers to the tract between the oropharyngeal tract and the anus. In more detail, the gastrointestinal tract refers to the mouth, pharynx, esophagous, stomach, small intestine (duodenum, jejunum), large intestine (cecum, colon, sigma and rectum) and/or anus.

According to a preferred aspect, the gastrointestinal tract refers to the esophagus, stomach or intestine.

According to another aspect, the diagnosis, prevention, alleviation, treatment and/or reduction of pathologies or disorders affecting the gastro-intestinal tract are inflammatory and/or degenerative pathologies preferably selected from inflammatory lesions, dysplasias, neoplasias and/or complications occurred during or after an endoscopic procedure. In more detail, such inflammatory and/or degenerative diseases can be selected from Barrett's esophagous, pre-neoplastic formations, neoplastic formations, tumors, polyps, adenomas, serrated lesions, ulcerations, stenosis, strictures, varices, gastroesophageal reflux diseases (GERD), esophagitis, haemorrhoids, fistulae, rhagades, motility alterations, esophageal cancer, esophageal ulcer, esophageal dysplasia, esophageal stenosis, esophageal varices, colon varices, inflammatory bowel disease, herbatum, acid ingestion, sour stomach, upset stomach, local anesthesia, and/or colon cancer. According to another preferred aspect, in case of an inflammatory lesions occurred during or after a resection procedure (such as for example ablation, polypectomy, EMR, ESD) the composition of the invention is locally injected in the artificial ulcer which is created by the resection procedure in the tissue and/or in its circumferential area though one or more circular or semi-circular in situ injections.

According to another preferred aspect, the inflammatory and/or degenerative diseases of the gastrointestinal tract are Barrett's esophagous, esophagitis, esophageal stenosis (stricture) and/or GERD.

According to another preferred aspect, the inflammatory and/or degenerative diseases of the gastrointestinal tract are haemorrhoids or fistulae.

According to another aspect, the liquid composition of the invention is for use in the diagnosis, prevention, alleviation, treatment and/or reduction of pathologies or disorders affecting the vagina or the bladder or the genitourinary tract more in general terms are preferably selected from bacterial infections, fungal infections, cancers, hormonal disorders and inflammations. More preferably, vaginitis, vaginal dryness, itching, burning, cystitis, menopausal disorders, candidiasis, herpes and cervical cancer.

According to another aspect, the liquid composition of the invention is for use in the diagnosis, prevention, alleviation, treatment and/or reduction of pathologies or disorders affecting the eyes or the ears are preferably selected from selected from bacterial infections, fungal infections, and inflammations. More preferably, ocular dryness, maculopathy, glaucoma and otitis.

According to another aspect, the liquid composition of the invention is for use in the diagnosis, prevention, alleviation, treatment and/or reduction of pathologies or disorders affecting the nose are preferably selected form sinusitis such as fungal sinusitis, rhinitis such as chronic atrophic rhinitis, vestibulitis, nasal congestion, histamine reactions and allergic disorders.

According to one aspect, the liquid compositions of the invention are administered via oral route.

According to another aspect, the liquid compositions of the invention are administered via rectal route.

According to another aspect, the liquid compositions of the invention are administered via vaginal route.

According to another aspect, the liquid compositions of the invention are administered via ocular route.

According to another aspect, the liquid compositions of the invention are administered via nasal route.

According to another aspect, the liquid compositions of the invention are administered via ear route According to another aspect, the liquid compositions of the invention are administered by injection. According to this aspect, local submucosal injection is performed injecting the liquid composition, preferably in emulsion or microemulsion, in situ in the pathological area tissue, in the lesion or in the circumferential area of the pathological area tissue or of the lesion through one or more circular or semi-circular injection/s in order to provide a controlled release of the drug to achieve a long acting response.

According to the invention, the number of the local injections can vary depending on the type of the pathology or disorder.

In all these aspects the liquid composition of the invention is able to create a depot of the active substance ensuring a reservoir of the same leading to constant release, improved local bioavailability (at the site of injection) and prolonged efficacy.

The control of the release is achieved by a slow erosion of the depot, with a long-lasting diffusion of the drug into the tissue and/or into the sub-mucosal/mucosal layer. Therefore, the efficacy is so mainly related to a topical action of the active substance thus reducing or avoiding any systemic side-effect.

According to the invention herein disclosed, one main component of the aqueous phase of said pharmaceutical liquid composition may be water for injection (WFI).

In some aspects of the invention herein disclosed, said aqueous phase may comprise, in dissolved form, one or more inorganic salts selected form the group comprising, but not limited to: chlorides, bromides, iodides, phosphates, carbonates, bicarbonates, sulfates, nitrates and the like.

In some aspects, said aqueous phase may comprise, in dissolved form, one or more organic salts selected form the group comprising, but not limited to: citrates, maleates, fumarates, acetates, lactates and the like.

Any mixture of the above inorganic and organic salts may be used to form the appropriate liquid composition, generally to buffer the pH of the composition in suitable biocompatible ranges or to reach the osmotic pressure required by the biologic environment where it is administered, especially when injected.

In some aspects, the aqueous phase of the liquid composition herein disclosed may comprise an amount of one or more inorganic and/or organic salts or mixtures thereof such as to have a final liquid composition which is hypotonic.

In some aspects, the aqueous phase of the liquid composition herein disclosed may comprise an amount of one or more inorganic and/or organic salts or mixtures thereof such as to have a final liquid composition which is isotonic.

In some aspects, the aqueous phase of the I liquid composition herein disclosed may comprise an amount of one or more inorganic and/or organic salts or mixtures thereof such as to have a final liquid composition which is hypertonic.

According to the invention herein disclosed, said inorganic and/or organic salts or mixtures thereof may be present in an amount ranging from 0% to 5% by weight with respect to the weight of the aqueous phase, more preferably from 0.1% to 4% by weight with respect to the weight of the aqueous phase, much more preferably from 0.4% to 3% by weight with respect to the weight of the aqueous phase. In a preferred aspect, the aqueous phase of said liquid composition contains sodium chloride dissolved.

According to the latter aspect, said sodium chloride is present in an amount ranging from 0% to 5% by weight with respect to the weight of the aqueous phase, more preferably from 0.1% to 4% by weight with respect to the weight of the aqueous phase, much more preferably from 0.4% to 3% by weight with respect to the weight of the aqueous phase.

In some aspects, the aqueous phase of the liquid composition herein disclosed comprises a buffer.

In some aspects, said buffer is a phosphate buffer.

In some aspects, said buffer is a citrate buffer. In some aspects, said buffer is a bicarbonate buffer. In a preferred aspect, said buffer is a phosphate buffer added with one or more inorganic salts unable to buffer the pH.

According to the latter aspect, the concentration of said phosphate buffer and said inorganic salts unable to buffer the pH is such as to have an aqueous phase which is phosphate buffered saline (PBS). Several compositions and preparation methods of PBS are well known in the art. According to the invention herein disclosed, the pH value of the pharmaceutical liquid composition ranges from about 4.0 to about 10.0, more preferably from about 4.5 to about 8.5, much more preferably from about 5.0 to about 8.0.

According to the invention, the pH value of said pharmaceutical liquid composition may be adjusted within the desired range by common techniques well known in the art, such as, for example, the addition of physiologically acceptable bases and/or acids.

According to the invention herein disclosed, said oily phase comprises at least one lipophilic compound.

In some aspects, said at least one lipophilic compound may be selected in the group of natural oils, comprising, but not limited to: almond oil, castor oil, corn oil, cottonseed oil, olive oil, safflower oil, sesame oil, soybean oil and the like.

In some aspects, said at least one lipophilic compound may be selected in the group of fatty acid esters, comprising, but not limited to: isopropyl palmitate, isopropyl myristate, ethyl oleate and the like.

In some aspects, said at least one lipophilic compound may be selected in the group of fatty alcohols, comprising, but not limited to: myristic alcohol, oleyl alcohol and the like.

In some aspects, said at least one lipophilic compound may be selected in the group of fatty acids, comprising, but not limited to: myristic acid, oleyl acid, palmitic acid and the like.

In some aspects, said at least one lipophilic compound may be selected in the group of triglycerides, such as long and/or medium-chain triglycerides and the like.

In some aspects, said at least one lipophilic compound may be selected in the group of diglycerides.

In some aspects, said at least one lipophilic compound may be selected in the group of monoglycerides.

Any mixture of the above lipophilic compounds can be used to form the appropriate liquid composition.

In an aspect, the lipophilic compound of said oily phase is sesame oil.

In another aspect, the lipophilic compound of said oily phase is ethyl oleate.

In another aspect, the lipophilic compounds of said oily phase are medium-chain triglycerides. In a preferred aspect, the lipophilic compound of said oily phase is soybean oil.

According to the invention herein disclosed, the oily phase of said liquid composition ranges from about 0.001% to about 20% by weight of the liquid composition, preferably from about 0.01% to about 15% by weight of the liquid composition, more preferably from about 0.02% to about 10% by weight of the liquid composition.

More preferably, said oily phase is contained in the composition of the invention in an amount of about 0.02% w/w or about 0.05% w/w or about 0.1% or about 1.0%, about 3.0%, or about 5.0% by weight, with respect to the weight of the composition.

The liquid composition of the invention herein disclosed may optionally comprise at least one co-surfactant. The addition of at least one co-surfactant to the mixture oily phase-surfactant-aqueous phase is advantageous since the co-surfactant acts in synergy with the surfactant in lowering the interfacial tension of the droplets of the dispersed phase of the liquid composition when in form of emulsion or microemulsion, with a stabilizing effect on the system. In the preparation of liquid compositions in form of emulsions or microemulsions according to the invention herein disclosed, said at least one co-surfactant can be selected in the groups comprising, but not limited to: low and medium chain alcohols, such as ethanol, propanol, isopropanol and the like; glycols, such as propylene glycol and the like; polyethylene glycols, such as PEG 200, PEG 300, PEG 400 and the like; DMSO; long chain alcohols, such as cetyl alcohol, myristyl alcohol, oleyl alcohol and the like; glycerol; low chain esters, such as ethyl acetate, ethyl lactate and the like; fatty acid esters, such as ethyl oleate, isopropyl myristate, isopropyl palmitate and the like; fatty acids, such as oleic acid, myristic acid and the like; salts of fatty acids, such as sodium oleate, sodium palmitate, sodium stearate and the like. Any mixture of the above co-surfactants can be used to form the appropriate liquid composition. In one aspect, the co-surfactant is propylene glycol. In another aspect, the co-surfactant is glycerol. In another aspect, the co-surfactant is sodium oleate. In a preferred aspect, the co-surfactant is a mixture of glycerol and sodium oleate.

According to the invention herein disclosed, said at least one co-surfactant is contained in an amount which ranges from about 0.00001% to about 3% by weight with respect to the weight of the liquid composition, preferably from about 0.00005% to about 0.05% by weight with respect to the weight of the liquid composition, more preferably from about 0.0001% to about 1.5% by weight with respect to the weight of the liquid composition.

The liquid composition of the invention herein disclosed may further comprise at least one agent characterized by having a trophic activity on the epithelial cells of the gastrointestinal mucosa.

Trophic agents are substances capable of promoting cellular growth, differentiation, and survival. In this sense, the incorporation into the liquid compositions according to the invention of at least one agent proved to possess a trophic activity on the epithelial cells of the gastrointestinal mucosa could be advantageous, since said liquid compositions could exert a positive, beneficial effect on wound healing, promoting cellular growth and differentiation for faster closure and wound healing of the surgical wound.

Additionally, at least one physiologically acceptable excipient may be added to the liquid composition according to the invention herein disclosed to obtain final composition provided with suitable characteristics and stability. By way of example, said at least one physiologically acceptable excipient may be selected among antioxidants, chelating agents, preservatives and/or antimicrobial agents.

Aspects of the present invention relate to the liquid composition as above disclosed and the liquid composition for use as a delivery vehicle in humans.

Aspects of the present invention relate to the liquid composition as above disclosed for use in diagnosing, treating, alleviating, reducing and/or preventing pathologies or disorders affecting the human body.

The delivery vehicle according to the present invention is able to control the release of the at least one active substance at the administration site due to the long-lasting diffusion of the active substance from the liquid composition of the present invention into the tissue and/or into the sub-mucosal/mucosal layer of the administration site.

In one aspect, said at least one active substance is cellular material, including cells and or cell components.

One particular use of the composition according to the present invention relates to the delivery of cells and or cell components, comprising but not limited to microvescicles, genomic material and lysosome. The cells can be differentiated cells derived from ectoderm, comprising but not limited to skin cells and melanocytes; endoderm, comprising but not limited to alveolar cells and pancreatic cells; and mesoderm, comprising but not limited to cardiac muscle cells and skeletal muscle cells; or stem cells such as embryonic stem cells, tissue-specific stem cells, mesenchymal stem cells and induced pluripotent stem cells, preferably mesenchymal stem cells (MSCs).

The cells required to be delivered to an individual patient can be added to the delivery vehicle immediately prior to administration in a clinical setting.

Mesenchymal stem cells (MSCs) possess unique properties that may make them a good option for treatment a lot of pathologies. Unlike other adult stem cells, they appear to escape allo-recognition by the immune system and they have immune-modulating properties, which allows them to be considered for use as an allogeneic cell therapy product.

The use of mesenchymal stem cells (MSCs) as clinical therapeutics is a relatively new avenue of study for treatment of a variety of diseases but there is a large and growing body of preclinical and early clinical experience with MSC therapy that shows great potential of stem cell therapy to promote the repair of damaged tissues.

The therapeutic impact of the MSCs is based upon their multiplicities of function and interaction with host tissues. MSCs have anti-inflammatory, regenerative and differentiated properties that could improve outcomes in damaged tissues and inflammation process.

The principle ability of MSCs is to induce host response in the surrounding tissue. This host response can be applied to a variety of clinical scenarios not only through cell-cell interactions but also through production of bioactive secreted factors such as small proteins, chemokines, cytokines, and other cellular regulators.

These factors have the capacity to induce angiogenesis or blood vessel development, be chemotactic, and induce cellular recruitment. MSCs also have the capacity to differentiate with the implicated environment to regenerate tissue or accommodate host tissue in a cell specific manner.

Mesenchymal stem cells (MSCs) have become one of the most studied stem cells, especially toward the healing of diseased and damaged tissues and organs. MSCs can be readily isolated from a number of adult tissues by means of minimally invasive approaches. MSCs are capable of self-replication to many passages and, therefore, can potentially be expanded to sufficient numbers for tissue and organ regeneration.

MSCs can self-renew by dividing and can differentiate into multiple tissue including bone, cartilage, muscle and fat cells, and connective tissue.

The delivery of the MSCs is a crucial point in cell therapy in fact the composition of the material for delivery must take into account the biocompatibility with cells and with the features of the host tissue, Different solutions have been proposed to deliver the therapeutic cells such as degradable polymer scaffolds or hydrogels made from naturally occurring biopolymers are one kind of degradable scaffold that has the key characteristics.

Cell therapy is considered as a novel treatment and different types of cells have been studied for Neurodegenerative Diseases, Stroke, Spinal cord injury, Liver and Pancreatic diseases, Heart disease, Respiratory diseases, Graft-versus-host disease, Kidney disease, Bone diseases, Chronic wounds and Inflammatory bowel disease, Otolaryngology head and neck surgery.

Some of the initial trials combined stem cells with glue. However, the addition of glue did not offer an advantage, and it was later observed that glue compromised the viability of the cells. Therefore, in more recent trials, stem cells have been injected only in a suspension with media.

Therefore, there is the need for an improved vehicle for cell therapy, which has to deliver the cells and promote their residence into the target site, meanwhile being biocompatible and fully re-absorbable within a certain time period.

The present invention provides such an improved vehicle.

The vehicle described herein can be used for delivery of the many different cells types to achieve different tissue structures such as bone cells, chondrocytes, epithelial cells, muscle cells, secretory cells, adipose cells and specially mesenchymal stem cells.

In one aspect, said cells include cells derived from ectoderm, endoderm and mesoderm or stem cells, such as embryonic stem cells, tissue-specific stem cells, mesenchymal stem cells and induced pluripotent stem cells, preferably mesenchymal stem cells (MSCs).

A suspension composing the delivery vehicle of the present invention and cells can be used for different diseases such as: neurodegenerative diseases, stroke, spinal cord injury, liver and pancreatic diseases, heart disease, respiratory diseases, graft-versus-host disease, kidney disease, bone diseases, chronic wounds, inflammatory bowel disease, otolaryngology head and neck surgery.

The sites and the number of cells to be implanted are dependent on the individual need and on the specific pathology.

The composition of the invention may contain suspended cells at a concentration of between about 0.5 and 50 million cells/ml, and the resulting cell suspension in the composition of the invention could be injected through systemic routes such as enteral and parenteral and local routes.

The cells mixed with the vehicle should be administrated within a period not exceeding eight hours if maintained from 4° C. to 37° C., preferably not exceeding six hours.

The cell suspension in the composition of the invention could be injected via a syringe or specific instrumentation with or without needle, to be suitably selected based on the site of administration/application, directly into a specific area.

The cell suspension in the composition of the invention can be used for intestinal disease including inflammatory bowel disease, short gut syndrome and irradiation damage.

For lesions such as anal and rectovaginal fistula, the cell suspension in the composition of the invention can be administered into the walls of the fistula and directly into its lumen (channel).

The cell suspension in the composition of the invention can be injected in the region of the gastroesophageal tract for the correcting of gastroesophageal reflux or can be injected in the ulcerative lesions of the digestive system.

Voiding dysfunction represents a diverse spectrum of urologic conditions including stress urinary incontinence, overactive bladder and vesico-ureteral reflux. Therefore, in one aspect, the cell suspension in the composition of the invention can be injected in urethral sphincter through a cystoscopic needle for a treatment of these dysfunctions.

In high potential-regenerative organs such as liver and pancreas, the cell suspension in the composition of the invention can be injected in specific areas to stimulate and regenerate the organ.

For example, in liver disease the cell suspension in the composition of the invention can be used to regenerate the liver tissue in the diseases such as: cirrhosis, alcoholic liver disease, alcoholic hepatitis, inflammatory disease.

In an orthopedic setting, the cell suspension in the composition of the invention can be injected into damaged cartilage such as articular cartilage injury, meniscal and rotor cuff damage, tendon injuries such as Achilles tendon or anterior cruciate ligament and bone lesions of the entire skeleton.

In cardiovascular repair the cell suspension in the composition of the invention can be injected in specific areas to support and to regenerate necrotic tissue.

Skin wound healing is a complex process necessitating the interplay between various populations of cells; in one aspect, the cell suspension in the composition of the invention is topically applied in wounded and/or lesioned skin to repopulate the dermis either as the mesenchymal component of skin equivalent constructs or more directly delivered in the wound to generate dermis.

Cells included in the vehicle for delivery can secrete growth factors to promote hair growth. The cell suspension in the composition of the invention can be injected into the scalp to regenerate hair in alopecia.

The cell suspension in the composition of the invention can be used in various degrees of alveolar bone resorption occur after tooth loss/extraction due to periodontal disease, severe caries, root fractures or accidental trauma.

In otolaryngology and "head and neck" diseases such as ear nose and throat diseases, maxillofacial surgery, periodontology, conservative dentistry and ocula diseases, the cell suspension in the composition of the invention can be used to restoration of a normal structure and function.

The loss of retinal neurons, their connections and supporting glia in ocular degenerative diseases causes permanent blindness, principally because lost photoreceptors and retinal ganglion cells (RGCs) are not replaced and RGC axons fail to regenerate. The use of cells such as stem cells has proven potential as a cellular therapy for retinal degenerative conditions through replacement of lost cells in the eye and/or the release of growth factors into damaged neuropil. In one aspect, cell suspension in the composition of the invention can be injected to give a trophic support for neurons in the degenerate retina and to stimulate glia to indirectly help effect neural repair.

Depending on the preferred application, a composition according to the invention may comprise at least one thermo-responsive polymer, at least one ion-sensitive polymer and at least one bio-adhesive polymer. In one aspect the at least one thermo-responsive polymer may comprise poloxamer 407, the at least one ion-sensitive polymer may comprise sodium alginate and the at least one bio-adhesive polymer may comprise sodium carboxymethylcellulose.

In one aspect the composition comprises poloxamer 407, sodium alginate and sodium carboxymethylcellulose.

Optionally, poloxamer 407 may be present in an amount of about 0.1% to about 30% by weight with respect to the weight of the liquid composition, optionally in the range 0.2% to 25%, 0.3% to 25% with respect to the weight of the composition, preferably 15% by weight with respect to the weight of the composition.

Optionally, sodium alginate may be present in an amount of about 0.001% to about 10% by weight with respect to the weight of the composition, optionally in the range 0.005% to 5%, 0.01% to 2.0% by weight with respect to the weight of the composition, preferably 0.2% (w/w) with respect to the weight of the composition.

Optionally, sodium carboxymethylcellulose is present in an amount of about 0.001% to about 10% by weight with respect to the weight of the composition, optionally in the range 0.005% to 5%, 0.01% to 2.0% by weight with respect to the weight of the composition, preferably 0.05% to 0.1% by weight with respect to the weight of the composition, and more preferably 0.05% (w/w) with respect to the weight of the composition.

Such a composition may be used in a method of treatment, wherein the composition is formulated such that an active substance can be added at the time of administration of the composition. Depending on the desired application, optionally, the active substance added at the time of administration may comprise cellular material such as microvescicles, genomic material and lysosomes, differentiated cells derived from ectoderm, endoderm or mesoderm, or stem cells such as embryonic stem cells, tissue-specific stem cells, mesenchymal stem cells and induced pluripotent stem cells, preferably mesenchymal stem cells (MSCs). Optionally, in one aspect the active substance added at the time of administration comprises human skin fibroblasts.

Such a composition may be used as a delivery vehicle in humans.

Such a composition may be used in the diagnosis, prevention, alleviation, treatment and/or reduction of pathologies or disorders affecting the human body.

DEFINITIONS

References in the specification to "one embodiment", "an embodiment", "one aspect", "an aspect" and similar indicate that the described embodiment or aspect may include a particular aspect, feature, structure or characteristic. Moreover, such phrases may, but do not necessarily, refer to the same embodiment or aspect referred to in other portions of the specification. Further, when a particular aspect, feature, structure or characteristic is described in connection with an embodiment or aspect, it is within knowledge of a person skilled in the art to affect or connect said aspect, feature, structure or characteristic with other embodiment or aspect, whether or not explicitly described.

The singular forms "a", "an" and "the" include plural references unless the context clearly dictates otherwise. Thus, for example, a reference to "a compound" includes a plurality of such compounds. It is further noted that the claims may be drafted to exclude any optional element. As such, this statement is intended to serve as antecedent basis for the use of exclusive terminology, such as "soley", "only", and the like, in connection with the recitation of claims elements or use of a "negative" limitation.

The term "and/or" means anyone of the items, any combination of the items, or all the items with which this term is associated.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics (and optionally physiologically acceptable excipients and/or adjuvants) of the invention are included.

The terms "consists of", "consisting of" are to be construed as a closed term.

PEG: Polyethylene glycol.
GG: Gellan gum
PLX: Poloxamers
HPC: Hydroxypropyl cellulose
HPMC: hydroxypropylmethylcellulose MC: Methyl cellulose
PBS: Phosphate buffered Saline
BHA: Buthyl hydroxyanisole
WFI: Water for injection
MTT: 3-(4,5-dimethylthiazol-2-yl)-2,5-diphenyltetrazolium bromide.

Unless indicated otherwise herein, the term "about" is intended to include values, e.g. weight percentages, proximate to the recited range that are equivalent in terms of the functionality of the individual ingredient, the composition, or the embodiment.

A person skilled in the art will recognize that, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range.

A person skilled in the art will recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of anyone or more of members of a recited group. Accordingly, provisos may apply to any of the disclosed categories or embodiments whereby anyone or more of the recited elements, species, or embodiments, may be excluded from such categories or embodiments, for example, as used in an explicit negative limitation.

The term "alleviating" refers to relieving the symptoms and/or manifestations of inflammatory and/or degenerative diseases of the gastrointestinal tract.

The term "reducing" refers to decreasing the extent of the damage caused by inflammatory and/or degenerative diseases of the gastrointestinal tract or to decreasing clinical signs or symptoms associated with such damage.

The term "Emulsion" refers to a heterogeneous preparation composed of two immiscible liquids (by convention described as oil and water), one of which is dispersed as fine droplets uniformly throughout the other. The phase present as small droplets is called the disperse, dispersed, or internal phase and the supporting liquid is known as the continuous or external phase. Emulsions are conveniently classified as oil-in-water (o/w) or water-in-oil (w/o), depending on whether the continuous phase is aqueous or oily. Multiple emulsions, which are prepared from oil and water by the reemulsification of an existing emulsion so as to provide two dispersed phases, are also of pharmaceutical interest. Multiple emulsions of the oil-in-water-in-oil (o/w/o) type are w/o emulsions in which the water globules themselves contain dispersed oil globules; conversely, water-in-oil-in-water (w/o/w) emulsions are those where the internal and external aqueous phases are separated by the oil. "Microemulsions" are thermodynamically stable, transparent (or translucent) dispersions of oil and water that are stabilized by an interfacial film of surfactant molecules. The surfactant may be pure, a mixture, or combined with a cosurfactant such as a medium-chain alcohol. Microemulsions are readily distinguished from normal emulsions by their transparency, their low viscosity, and more fundamentally their thermodynamic stability and ability to form spontaneously. The dividing line, however, between the size of a swollen micelle (~10-140 nm) and a fine emulsion droplet (100-600 nm) is not well defined, although microemulsions are very labile systems and a microemulsion droplet may disappear within a fraction of a second whilst another droplet forms spontaneously elsewhere in the system. The above definitions of "emulsion" and "microemulsion" were taken from "Encyclopedia of Pharmaceutical Technology", 3rd edition, Informa Healtcare.

The term "endoscopic mucosal resection" (EMR) refers to an endoscopic technique developed for removal of sessile or flat neoplasms confined to the superficial layers (mucosa and submucosa) of the GI tract. The term "endoscopic mucosal dissection" (ESD) refers to an endoscopic technique developed specifically for removing larger lesions.

"Endoscopic injection needles", known also under the names "injection needles" or "injection needle catheters" or "endoscopic injection needle catheters", are devices which can be long up to about 230 cm and which include a relatively long catheter within which an inner injection tube having a distal Injection needle is slideably disposed. Generally, a proximal actuating handle is coupled to the catheter and the injection tube for moving one relative to the other when necessary. The needle is generally retractable. Fluid access to the injection tube is typically provided via a luer connector on the handle. Endoscopic injection needle devices are typically delivered to the injection site through the working channel of the endoscope. In order to protect the lumen of the endoscope working channel from damage, the handle of the infusion needle device is manipulated to withdraw the distal Injection needle into the lumen of the catheter before inserting the device into the endoscope. This is important to prevent exposure of the sharp point of the injection needle as the device is moved through the lumen of the endoscope. When the distal end of the endoscopic injection needle device is located at the injection site, its handle is again manipulated to move the injection needle distally out of the lumen of the catheter. When advanced to the most distal position, the exposed portion of the injection needle is approximately 4-6 mm in length.

The "viscosity" defines the resistance of a liquid or semisolid against flow. The flow of liquids or semisolids is described by viscosity, or, more precisely, by shear viscosity η. The shear viscosity of a fluid expresses its resistance to shearing flows, where adjacent layers move parallel to each other with different speeds. Common units of measurement of viscosity are the pascal-second (Pa·s), the poise (P) and cP (centipoises).

"Modulus G'" refers to elastic or storage modulus obtained in dynamic regimen. An elastic modulus (also known as modulus of elasticity) is a number that measures an object or substance's resistance to being deformed elastically (i.e., non-permanently) when a stress is applied to it. The elastic modulus of an object is defined as the slope of its stress-strain curve in the elastic deformation region.

"Cellular material" refers to cells and/or cell components.

"Body temperature" refers to the level of heat produced and sustained by the body processes. Heat is generated within the body through metabolism of nutrients and lost from the body surface through radiation, convection, and evaporation of perspiration. Heat production and loss are regulated and controlled in the hypothalamus and brainstem. Normal adult body temperature, as measured orally, is 37° C., even though little variations are normally recorded throughout the day.

"Room temperature" (RT) is generally defined as the ambient air temperature in whatever environment being used for a given procedure. More specifically, it is defined as 20-25° C., as some ambient temperatures, by nature, do not fall within this range. Generally, protocols calling for steps to be performed at RT require that temperatures do not fall below 18° C., and do not exceed 27° C.

"In (or under) laboratory test conditions" or "in laboratory conditions" or "in laboratory tests", as used herein, refer to in-vitro conditions, such as methods, equipment and instruments commonly used in laboratory tests to perform a physical-chemical characterisation of a composition. The term refers to methods, equipment and instruments used and performed in laboratory.

"Pa·s" Pascal-second, unit for measuring viscosity

"P" Poise, unit for measuring viscosity

"cP": centipoises, unit for measuring viscosity.

The following examples are included for purpose of illustration of certain aspects and aspects of the invention, and are not intended to limit the invention.

EXAMPLES

Example 1—Microemulsion

| Component(s) | % w/v |
|---|---|
| Budesonide | 0.050 |
| Poloxamer 188 | 12.000 |
| Sodium Alginate | 0.200 |
| Medium Chain Triglycerides | 0.570 |
| Polyoxyl-15-Hydroxystearate | 3.500 |
| PolyEthylen Glycol (PEG) 400 | 1.160 |
| Ethanol | 0.590 |
| Sodium Hydroxide | 0.0012 |
| WFI | up to 100 |

In a suitable vessel, polyoxyl 15-hydroxystearate is heated to 60° C. under stirring, until a homogeneous melted substance is obtained; Budesonide is then added under stirring, keeping the temperature at 60° C. Medium chain triglyceride and PEG 400 are then added under stirring until complete dissolution of Budesonide is obtained (Phase A).

An amount of the total amount of WFI (4-20%) is poured into phase A under stirring (T=60° C.); when a homogeneous mixture is obtained, the temperature is lowered to RT; ethanol is then added under stirring until homogeneous mixture is obtained (phase B).

In the main vessel, the remaining amount of WFI (80-96%) is poured. Then Phase B is added drop-wise under vigorous stirring. Poloxamer 188 is then added under vigorous stirring until a complete dissolution of the polymer is obtained. At the end of Poloxamer dissolution, Sodium Alginate is added under vigorous stirring until a complete dissolution of the polymer is obtained (Phase C).

At the end of the addition Sodium Hydroxide is added up to pH 6. and the mixture is stirred until complete dissolution (phase D).

The mixture is brought to final volume adding WFI. The mixture is kept under stirring until homogeneity is obtained. The application of such a composition can be easily done by drinking a small volume of the composition, aimed to bio-adhere to the esophagous and to the stomach mucosa, in order to be active for esophagitis and Barrett esophagous. In the alternative, the composition could be also administered by injection, such as submucosal injection or in a catheter inserted in a gastroscope.

Example 2 Emulsion

| Component | % w/v |
|---|---|
| Budesonide | 0.005 |
| Poloxamer 188 | 12.000 |
| Alginic acid | 0.200 |
| Medium chain triglycerides | 1.000 |
| Polyoxyl 15-hydroxystearate | 4.000 |
| Sodium chloride | 0.450 |
| Butylated hydroxyanisole (BHA) | 0.100 |
| WFI | up. to 100 mL |

In a suitable vessel, polyoxyl 15-hydroxystearate is heated to 60° C. under stirring, until a homogeneous melted substance is obtained; medium chain triglycerides are then added under stirring. Budesonide and butylated hydroxyanisole (BHA) are added to the above mixture under stirring, keeping the temperature at 60° C. The mixture is stirred until complete dissolution of budesonide is obtained (Phase A).

An amount of the total amount of WFI (4-20%) is poured into phase A under stirring (T=60° C.); when a homogeneous mixture is obtained, the temperature is lowered to RT (phase B).

In another vessel, the remaining amount of WFI (80-96%) is poured, and it is heated at 60° C.

Poloxamer 188 is added under stirring, and the mixture is stirred until a complete dissolution of the polymer is obtained (T=60° C.) (Phase C).

Phase B is added drop-wise to phase C under vigorous stirring (T=60° C.). At the end of the addition, the temperature is cooled down to RT, then, alginic acid and sodium chloride are added and the mixture is stirred until complete dissolution (phase D).

The mixture is brought to final volume adding WFI. The mixture is kept under stirring until homogeneity is obtained. The application of such a composition can be easily done by drinking a small volume of the composition, aimed to bio-adhere to the esophagous and to the stomach mucosa. In the alternative, the composition could be also administered by injection, such as submucosal injection or in a catheter inserted in a gastroscope.

Example 3—Emulsion

| Component | % w/w |
|---|---|
| Budesonide | 0.020 |
| Norepinephrine hydrochloride | 0.010 |
| Poloxamer 407 | 15.000 |
| Sodium alginate | 0.200 |
| Soybean oil | 0.500 |
| Glycerol | 0.016 |
| Phosphatidylcoline | 0.075 |
| Sodium oleate | 0.0019 |
| PBS | 0.500 |
| WFI | up to 100 |

The manufacture of the composition is described hereinafter:
 a) In a suitable vessel provided with a stirrer, WFI (90% of the total amount) is loaded; then, is cooled at a temperature ranging between 5° C. and 20° C.; then, poloxamer 407 is added under stirring. The mixture is kept under stirring until a complete dissolution is achieved and then heated up to room temperature (Phase A).

b) In a suitable vessel provided with a stirrer, about 0.02% of the total amount of WFI is loaded; the temperature is raised at 60° C. Phosphatidylcholine, glycerol and sodium oleate are added under stirring. The stirrer is operated until a complete homogenization is achieved (Phase B).

c) In another vessel, budesonide is added to soybean oil under stirring at a temperature of 60° C.; the mixture is kept under stirring at 60° C. until a complete dissolution is obtained (Phase C).

d) Phase C is added to Phase B under stirring at 60° C. The mixture is kept at T=60° C. under stirring until an homogeneous emulsion is obtained. The emulsion is then cooled at a room temperature (Phase D).

e) Phase D is added to Phase A under stirring. Then, norepinephrine hydrochloride and PBS (prepared according to well-known conventional receipts) are added under stirring. The mixture is kept under stirring until homogeneity.

f) At the end of the addition, sodium alginate is added under vigorous stirring until complete dissolution is obtained;

The mixture is brought to the final weight adding WFI. The mixture is kept under stirring until homogeneity is obtained. The application of such a composition can be easily done by drinking a small volume of the composition, aimed to bio-adhere to the esophagous and to the stomach mucosa. In the alternative, the composition could be also administered by injection, such as submucosal injection or in a catheter inserted in a gastroscope Example 4—Microemulsion

| Component | % w/v |
| --- | --- |
| Flurbiprofen | 0.005 |
| Poloxamer 188 | 10.000 |
| Sodium alginate | 0.400 |
| Medium chain triglycerides | 1.000 |
| Polyoxyl 15-hydroxystearate | 4.000 |
| PBS | 0.450 |
| BHA | 0.100 |
| WFI | q.s. to 100 mL |

The manufacturing process and the administration way of example 4 are similar to that of example 1.

Example 5 Water-Based Solution

| Component(s) | % w/w |
| --- | --- |
| Poloxamer 407 | 13.500 |
| Pectin | 0.500 |
| Sodium Carboxymethylcellulose | 0.100 |
| Sodium Alginate | 0.500 |
| Citric acid monohydrate | 0.250 |
| Sodium citrate dihydrate | 0.513 |
| Potassium Sorbate | 0.100 |
| Sodium benzoate | 0.100 |
| Sucralose | 0.100 |
| Flavouring agents | 0.500 |
| Purified water up to | 100.00 |

In a suitable vessel provided with a stirrer, Purified water (95% of the total amount) is loaded; then, Sodium benzoate is added under stirring. The mixture is kept under stirring until a complete dissolution is achieved Potassium Sorbate is then added under stirring until complete dissolution is achieved.

Poloxamer is added to the above mixture under vigorous stirring until complete dissolution is obtained.

Then Sodium alginate is added to the mixture above under stirring until a homogeneous mixture is obtained.

Pectin is then added to the mixture above under stirring until a homogeneous mixture is achieved. Then Sodium carboxymethylcellulose is added to the mixture above under stirring until a homogeneous mixture is obtained.

Sodium citrate and citric acid are then added to the mixture above under stirring until a homogeneous mixture is achieved.

At the end of the addition, sucralose and flavouring agents are added under stirring until complete dissolution is obtained.

The mixture is brought to final weight adding Purified water. The mixture is kept under stirring until homogeneity is obtained. The application of such a composition can be easily done by drinking a small volume of the composition, aimed to bio-adhere to the esophagous and to the stomach mucosa.

Example 6 Water-Based Solution

A vehicle intended for application on esophagus walls via oral route is prepared.

| Component(s) | % w/w |
| --- | --- |
| Poloxamer 407 | 13.500 |
| Pectin | 0.500 |
| Sodium Carboxymethylcellulose | 0.100 |
| Sodium Alginate | 0.500 |
| Potassium sorbate | 0.100 |
| Sodium benzoate | 0.100 |
| Sucralose | 0.100 |
| Flavouring agents | 0.500 |
| Purified water up to | 100.00 |

The manufacturing process of example 6 and the administration way are similar to that of example 5.

The liquid composition is then packed in vials containing 10 mL or 20 mL of composition.

Prior to administration a powder mixture composed by Sodium Bicarbonate, Calcium Carbonate, Magnesium Oxide and mannitol is loaded into a plug and plunger single dose shaker system. Screwing the cap the powder drops into the vehicle then the vial is shaken well until a homogeneous suspension is obtained.

The application of such a composition can be easily done by drinking a small volume of the composition, aimed to bio-adhere to the esophagous and to the stomach mucosa.

Example 7 Water-Based Solution

| Component(s) | % w/w |
| --- | --- |
| Poloxamer 407 | 13.500 |
| Pectin | 0.500 |
| Sodium Carboxymethylcellulose | 0.100 |
| Citric acid monohydrate | 0.250 |
| Sodium citrate dihydrate | 0.513 |
| Potassium sorbate | 0.100 |
| Sodium benzoate | 0.100 |
| Sucralose | 0.100 |

-continued

| Component(s) | % w/w |
|---|---|
| Flavouring agents | 0.500 |
| Methylene Blue | 0.007 |
| Purified water up to | 100.00 |

The manufacturing process of example 7 and the administration way are similar to that of example 5. The application of such a composition can be easily done by drinking a small volume of the composition, aimed to bio-adhere to the esophagous and to the stomach mucosa. In such a case the drinking should be done around half an hour before GI endoscopy (esophagous or stomach) in order to achieve color contrast in the mucosal tissues in GI endoscopy.

Example 8 Water-Based Solution

| Component(s) | % w/w |
|---|---|
| Poloxamer407 | 16.000 |
| Sodium Alginate | 0.200 |
| Sodium Carboxymethylcellulose | 0.050 |
| WFI up to | 100.00 |

In a suitable vessel provided with a stirrer, Purified water (95% of the total amount) is loaded; then, is cooled at a temperature ranging between 5° C. and 20° C.; then, poloxamer 407 is added under stirring. The mixture is kept under stirring until a complete dissolution is achieved and then heated up to room temperature.

Then Sodium alginate is added to the mixture above under stirring until a homogeneous mixture is obtained.

Then Sodium carboxymethylcellulose is added to the mixture above under stirring until a homogeneous mixture is achieved.

The mixture is brought to final weight adding Purified water. The mixture is kept under stirring until homogeneity is obtained.

The application of such composition can be easily done by injection of a ready to use extemporaneous suspension of mesenchymal stem cells (MSC) in the vehicle.

The MSC suspension vehicle could be applied in urinary incontinence diseases, especially in the structural and functional restoration of the urethral sphincter.

After suspension, the biocompatibility in terms of viability and cytotoxicity has been tested and a functional test, such as migration of the MSC in such vehicle, has been performed.

Viability Test:

MSC were suspended in the vehicle of example 8, then testing the viability of the cells.

The viability test was performed on 120,000 cells per FACs tube in a total volume of 300 μl of the vehicle. The incubations were done both at 4° C. and 37° C. and analyzed after 2, 4, and 6 hours. In parallel, controls, defined as MSCs cultured in complete cell medium only, were analyzed at the same conditions of the MSC suspension vehicle.

Importantly, the time, from 2 h to 6 hours, simulates the interval within which the suspension can be administered. The temperatures instead, establish the stability/viability of the cells into vehicle if the suspension is maintained at low temperatures such as 4° C. before the administration or at physiological temperature such as the body temperature (37° C.).

The viability assay involved addition of 1 μg/mL of propidium iodide (PI) immediately before flow cytometric analyses. Dead cells have compromised membrane so they were stained by PI.

No difference was observed among cells viability in media vs cells viability resuspended in the MSC suspension vehicle both at 4° C. and at 37° C. An advantageous data was represented by the viability obtained at 37° C., in fact they were more live cells in MSC suspension vehicle relative to the media control. This event predicts what could happen to the cells when they reach the target site into the body (FIG. 1)

Citotoxicity Test: To better understand the biocompatibility of the vehicle of example 8 a cytotoxicity test was performed according to ISO 10993-5.

On Mesenchymal stem cells suspended in the vehicle the cytotoxicity test, with MTT assay, was performed.

The MTT (3-(4,5-dimethylthiazol-2-yl)-2,5-diphenyltetrazoliumbromid) is metabolically reduced in viable cells to a blue-violet insoluble formazan.

At 1st day the mesenchymal stem cell in culture were removed from culture flask by enzymatic digestion such as Tryple select (Gibco).

The cell suspension was centrifuged at 1400 rpm for 10 min and the pellet was suspended in complete culture medium at a density of $1 \times 10^4$ cells/100 μl.

100 μl of the cell suspension were dispensed into wells of a 96-well tissue culture plate and incubated for 24 h (5% CO2, 37° C., >90% humidity).

After 24 h incubation, the culture medium was aspired from the cells. Per well, 100 μl of medium containing the appropriate concentration of the vehicle to test, were added.

Five different concentrations of the MSC suspension vehicle were tested: 20%, 10%, 5%, 2.5% and 1.25% in complete medium culture. The cells were incubated for 24 h (5% CO2, 37° C., >90% humidity). After 24 h treatment, the culture medium was removed from the plates and 50 μl of the MTT solution was added to each well and the plate was incubated for 2 h in the incubator at 37° C. The MTT solution was diluted according to datasheet containing in In Vitro Toxicology Assay, MTT based Tox-1 (Sigma).

After the incubation time, the formazan crystals were solubilized by adding of 100 μl of MTT Solubilization Solution (In Vitro Toxicology Assay, MTT based Tox-1; Sigma).

After mixing in a gyratory shaker for the complete dissolution of the crystals, the measure of absorbance at a wavelength of 570 nm and the measure of the background absorbance at 690 nm were performed.

Figure 2:
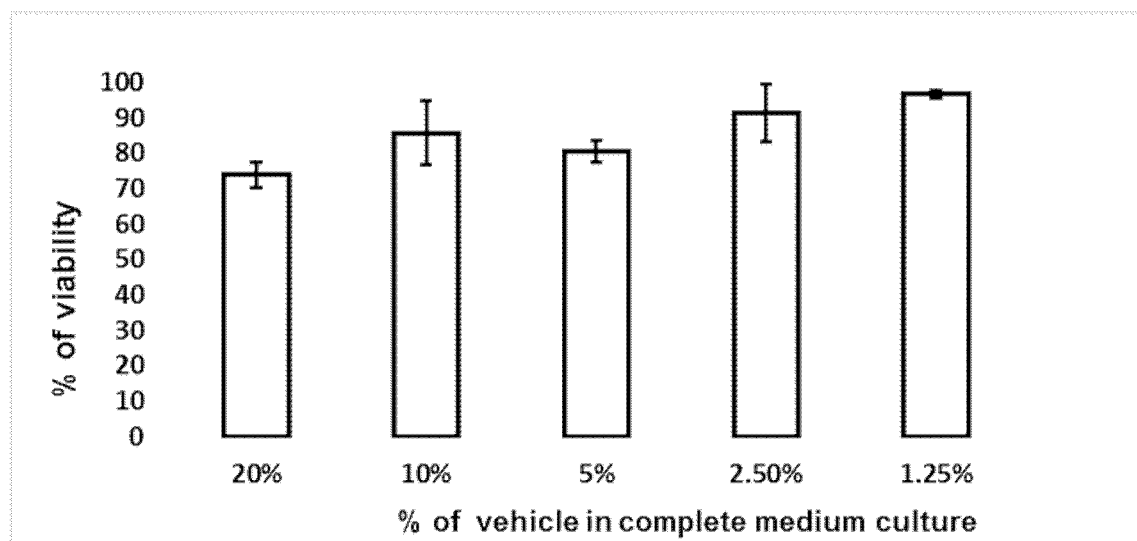
FIG. 2 reports the MTT assay on MSC at different concentrations of the MSC suspension vehicle.

A substance is not cytotoxic for values greater/equal than 70% of viability, and as shown in (FIG. 2) the viability for the vehicle after 24 h was always greater than 74%. This demonstrates that the MSC suspension vehicle is not cytotoxic for mesenchymal stem cells.

Cell Migration Assay:

In order to evaluate the suitability of the vehicle of example 8 as a delivery vehicle, cell migration was performed with Boyden chamber and imaged by fluorescence microscope.

Cell migration test that was selected for these experiments was the Boyden chamber, which is ideally suited for the quantitative analysis of different migratory responses of cells.

The classic Boyden Chamber system uses a hollow plastic chamber, sealed at one end with a porous membrane. For the induction of chemotactic response of cells, attractants were added to the lower compartment of the chamber.

In a standard Boyden assay, the pore diameter of the membrane is typically 3 to 12 µm, a pore size of 8 µm in 24-well plate, was selected since this dimension supports optimal migration for mesenchymal stem cells.

After preparation of migration chambers (8 µm) in 24-well plate, 100 µl of serum free medium in the chambers were added. After removal of serum, about $2 \times 10^5$ cells were mixed with a solution of medium and MSC suspension vehicle at different concentrations (75%, 80%, 85%, 90%, 95% and 100%) and put into migration chambers for to 2 hours at 37° C. with 5% $CO_2$.

The complete culture medium was added in control. A quantity equal to 750 µl culture medium with serum in lower chambers was added and incubate at 37° C. with 5% $CO_2$ for 24 h. The medium was removed from the chambers and the chambers were washed twice with PBS.

The cells were fixed with formaldehyde (3.7% in PBS) for 15' at room temperature. After washing twice with phosphate-buffered saline (PBS) the permeabilization was performed with 100% of methanol at room temperature for 30 minutes. The methanol was removed and a Giemsa or DAPI stain were performed to detect the cells captured into membrane.

Figure 3:
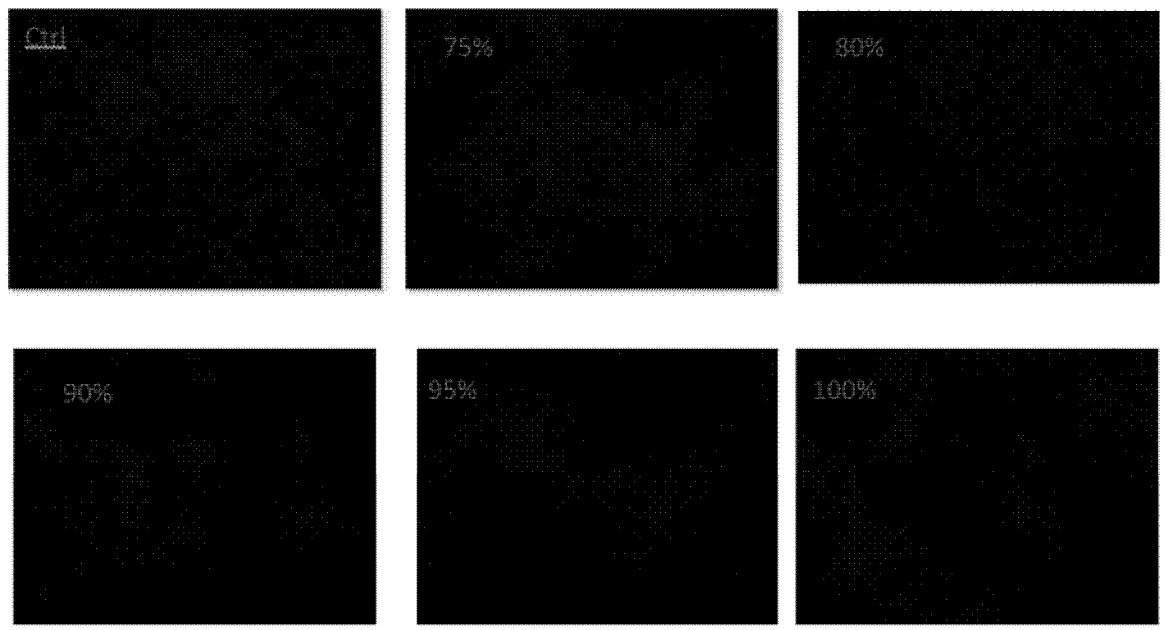
FIG. 3 shows (20× magnification) DAPI staining of Mesenchymal stem cells in Boyden chamber at different concentrations of MSC suspension vehicle. Top panels (from left to right control, 75%, 80%); Bottom panels (from left to right 90%, 95%, 100%).

The FIG. 3 with DAPI staining, shows the important property of the MSC suspension vehicle, in fact this composition does not inhibit cellular function such as a motility and allows the cells migration, therefore it predicts a cell motility once injected into a specific area into the body.

Figure 4:
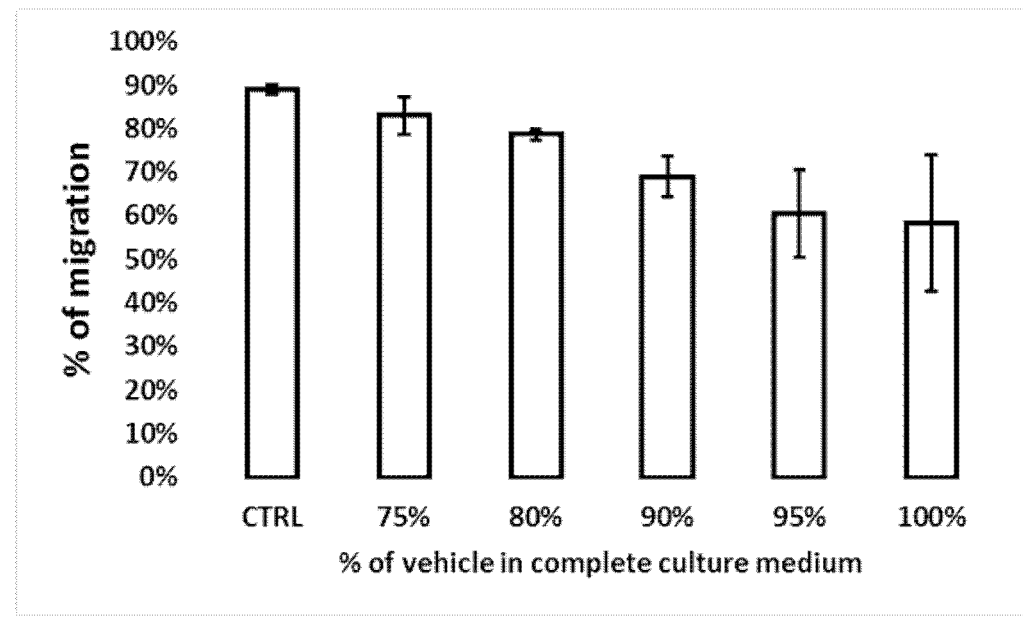
FIG. 4 reports % of migration of MSC in Boyden Chambers at different concentrations of MSC suspension vehicle.

Moreover, the obtained data indicated That about 60% of cells were able to migrate when the concentration of the vehicle was equal to 100%, When the dilution of the MSC suspension vehicle increased, simulating a normal "in vivo" mechanism of dilution, the migration value was comparable to the control, 83% Vs 89% (FIG. 4).

Example 8 Bis Water Based Solution (Injectable Cell Therapy)

Composition 7364/1

| Component(s) | % w/w |
| --- | --- |
| Poloxamer 407 | 15.000 |
| Sodium Alginate | 0.200 |
| Sodium Carboxymethylcellulose | 0.050 |
| WFI up to | 100.00 |

An example composition according to the invention as detailed in the present example was tested in an in vitro Wound healing test—Tissue Regeneration test.

INTRODUCTION

Liquid compositions of the invention can be used as vehicle in the field of cell therapy in order to heal skin injuries. Wound healing is a complex and dynamic process of replacing devitalized and missing cellular structures and tissue layers. There are a series of interdependent and overlapping phases in which a variety of cellular and matrix components act together to re-establish the integrity of damage tissue and replacement of lost tissue. The stages of wound healing proceed in an organized way and follow four processes: haemostasis, inflammation, proliferation and maturation. This cascade of events begins immediately after injury by the secretion into the local environment of a pool of growth factors, cytokines and proteins from serum and from the platelet activation. Platelets constitute a source of multiple growth factors and proteins involved in tissue regeneration. Many reports describe the efficacy of the platelet lysate as a substitute supplement for fetal bovine serum (FBS) in experimental and clinical cell culture for tissue regeneration.

An example composition according to the invention as detailed in the present example (also called 7364/1) has been tested in an *In vitro Wound healing test—Tissue Regeneration test*, and compared with a different liquid formulation.

The liquid formulation (also called 7386) which was used as reference vehicle for tissue regeneration is a composition disclosed in Sandri et al. "*An in Situ Gelling Buccal Spray Containing Platelet Lysate for the Treatment of Oral Mucositis*", Current Drug Discovery Technologies, 2011, 3, 277-285.

The reference vehicle composition is reported below:
Reference Vehicle Composition 7386

| Component(s) | % w/w |
| --- | --- |
| Poloxamer 407 | 14.000 |
| Sodium Alginate Low Viscosity | 0.200 |
| Saline solution (NaCl 0.9%) | Up to 100.00 |

The test has been carried out in order to assess the potential use of a composition according to the invention as a vehicle for tissue regeneration. Both the composition 7364/1 and the reference vehicle 7386, loaded with platelet lysate, have been tested in a simulate skin lesion, to study their effect on cell growth and on cellular regenerative capacity. Complete medium without serum was used as a control.

In Vitro Wound Healing Test

Human Skin Fibroblasts (HSF) at $5^{th}$ passage were used for the In vitro Wound Healing test. Dulbecco's modified Eagle medium (DMEM, Sigma Life Science) supplemented with 10% foetal bovine serum (FBS) (EuroClone, Milan, Italy) with 200 U/ml penicillin and 0.2 mg/ml streptomycin (Gibco by life technologies) was used as growth medium.

The human platelet lysate (PL) which was used in the test was produced by Red Cross in Ulm (Germany), obtained from a pool of no more than 16 healthy donors.

The cells were kept at 37° C. in a 5% $CO_2$ atmosphere with 95% of relative humidity.

In vitro wound healing test was carried out using a Petri µ-Dish (Ibidi, Giardini, Milan, Italy) in which an insert is enclosed. The insert is formed by 2 chambers with a growth area of 0.22 $cm^2$ dived by a septum with a cell-free gap of 500 µm±50 µm width.

The technique involves making a linear thin scratch "wound" (creating a gap) in a confluent cell monolayer, and subsequently capturing images of the cells filling the gap at regular time intervals. HSF were seeded in each chamber at $10^5$ cell/$cm^2$ in growth medium; after 24 h cells reached confluence and the insert was removed displaying 2 areas of cell layers divided from the prefixed gap.

A platelet lysate (PL) mixture was prepared mixing 190 µL of complete medium with 10 µL of Platelet Lysate (PL). Both the formulations; the formulation of Example 8 bis (test) which corresponds to a composition within the scope of the present invention (7364/1) and the formulation 7386 (reference vehicle), were diluted 1:20 with the PL mixture prepared as described above.

The obtained vehicles loaded with PL were seeded into the wells. Complete medium without serum was seeded as control.

At prefixed times (to, 24 h, 48 h and 72 h) microphotographs were taken to evaluate the cell growth in the gap as indicator of tissue regeneration.

Images were analysed using ImageJ Software for image analysis (NIH, Bethesda, MD).

Absolute wound density (AWD) and Relative wound density (RWD) was used to measure cell migration by ImageJ software. The software allow to detect the presence and the numerosity of cells within the gap through a greyscale applying the following formulas:

AWD=MGV $t$-IMV $t_0$

RWD=(MGV $t$-MGV $t_0$)/(MGV Ctrl $t$-MGV Ctrl $t_0$)

MGV=Mean Grey Value
t=prefixed time
$t_0$=starting time point
Ctrl=control (medium without serum)

In Table 1 the results of the experiments are reported; for each time point, Three photographs were collected and analysed, Averages and Standard Deviations are reported.

TABLE 1

Mean Grey Values obtained for all considered samples at each time-point.

| | | Medium (CTRL) MGV | Reference Vehicle Medium + PL + 7386 MGV | Composition of Example 8bis Medium + PL + 7364/1 MGV |
|---|---|---|---|---|
| t0 | | | 16607 | 18000 | 16783 |
| t24 | | | 33874 | 34809 | 49857 |
| | | | 35721 | 36348 | 54942 |
| | | | 40275 | 42753 | 60690 |
| | AVERAGE | | 36623 | 37970 | 55163 |
| | SD | | 3295 | 4213 | 5420 |
| | AWD(t24 − t0) | | 20016 | 19970 | 38380 |
| t48 | | | 32032 | 35523 | 61868 |
| | | | 27602 | 54314 | 61584 |
| | | | 29958 | 37254 | 60119 |
| | AVERAGE | | 29864 | 42364 | 61190 |
| | SD | | 2216 | 10385 | 939 |
| | AWD(t48 − t0) | | 13257 | 24364 | 44407 |
| t72 | | | 43835 | 50593 | 54100 |
| | | | 28719 | 62511 | 62814 |
| | | | 33199 | 63403 | 71276 |
| | AVERAGE | | 35251 | 58836 | 62730 |
| | SD | | 7764 | 7152 | 8588 |
| | AWD(t72 − t0) | | 18644 | 40836 | 45947 |

Figure 10:
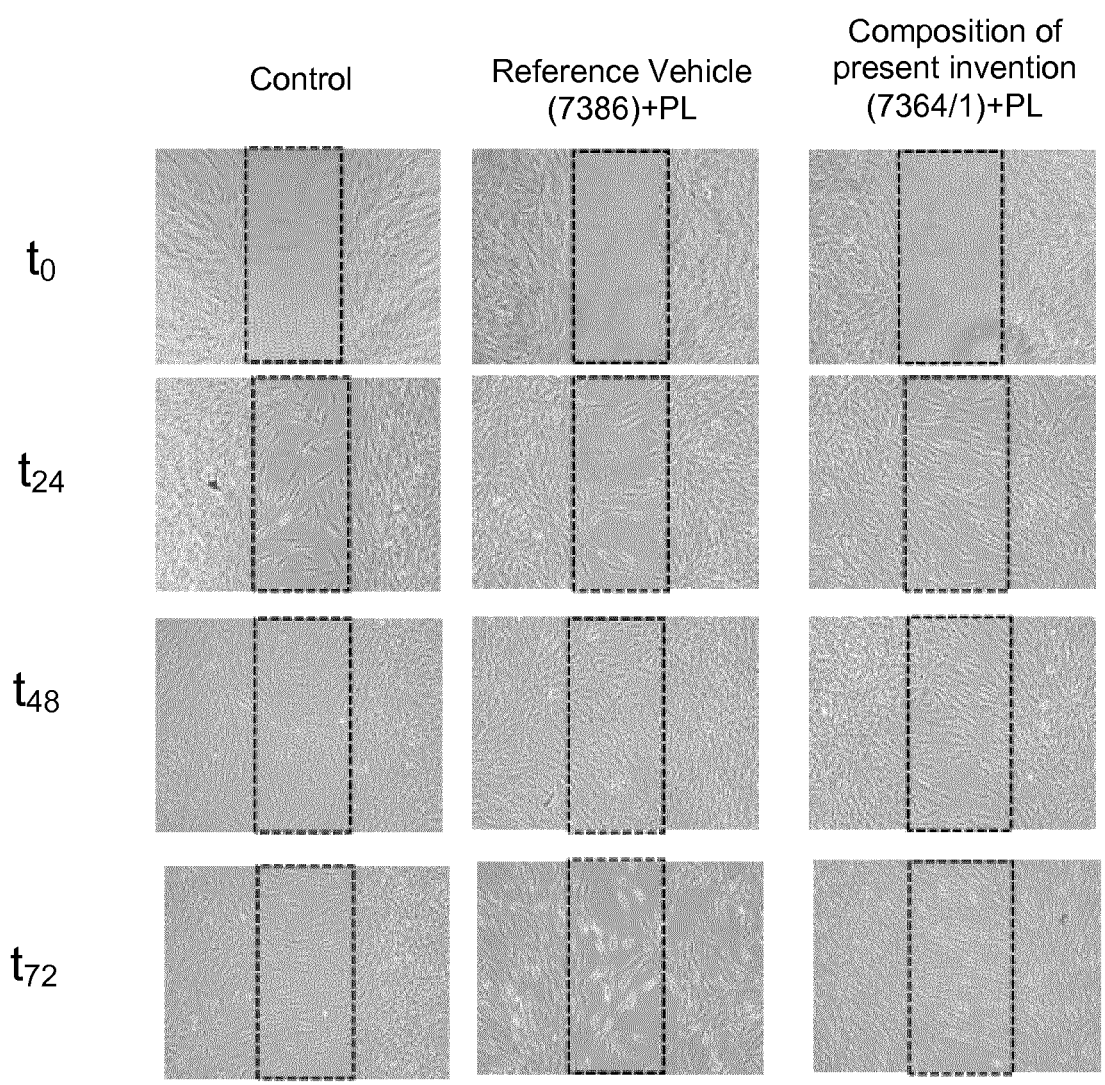
FIG. 10 shows the evolution of the wound area of all tested samples over time. 10× images of the samples after different time points (t0, t24, t48 and t72) are presented. The black rectangle circumscribes the wound area.

FIG. 10 shows the evolution of the wound area of all tested samples over time. 10× images of the samples after different time points (t0, t24, t48 and t72) are presented. The black rectangle circumscribes the wound area.

Table 2 shows the RWD of the formulations under test with respect to the relevant control,

TABLE 2

RWD compared to control.

| | Medium + PL + 7386 | Medium + PL + 7364/1 |
|---|---|---|
| t24 | 1.00 | 1.92 |
| t48 | 1.84 | 3.35 |
| t72 | 2.19 | 2.46 |

At time 0, after inserts removal, cell free gaps, or wound gaps, were evident for all the samples: medium without serum (Control), formulation 7386 (reference vehicle) with PL and formulation 7364/1 (a composition within the scope of the present invention) with PL.

After 24 h in all the samples a reduction of a cell free area was observed. Several cell bridges are present both in the control and in the two vehicles under test, even though some intercellular spaces were yet evident. As shown in Table 2, a composition within the scope of the present invention, loaded with PL, exhibited wound regeneration around 2 times higher than Control.

After 48 h an increase in MGV value was obtained in all the samples under test. The composition of the present invention with PL showed a RWD ratio 3 times higher than the Control, and no cells morphology differences with respect to Control condition were observed. Meanwhile the reference vehicle with PL showed an increase 2 times higher than Control.

Figure 11:
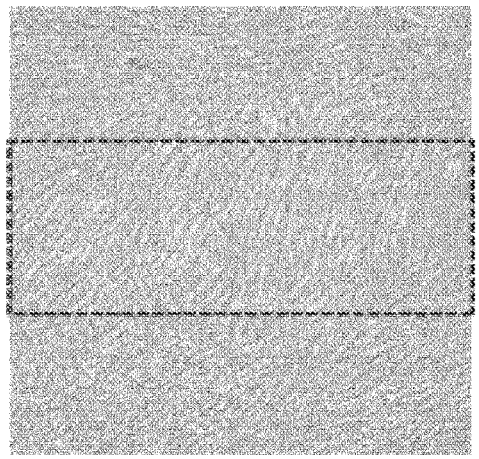
FIG. 11 shows a comparison of Control, Reference Vehicle (7386)+PL and (7364/1)+PL samples after 72 h. 10× images of the samples after 72 h are presented. The black rectangle circumscribes the wound area.
Figure 11:
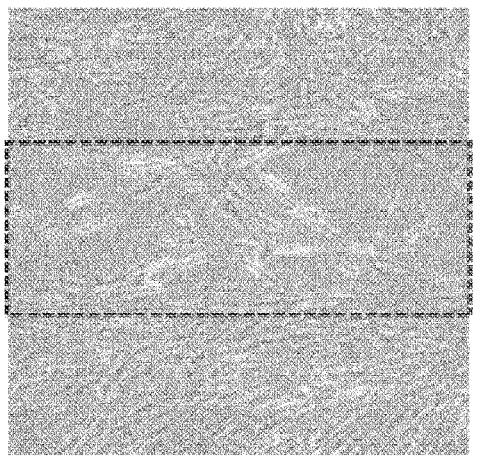
Figure 11:
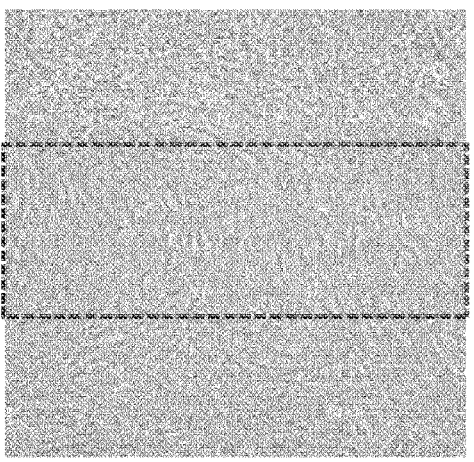

At 72 h, as shown in FIG. 11, it was possible to see the complete migration of cells into the free gap and for the example composition of the present invention with PL the RWD, in the wound gap, was about 2.5 times compared to Control while for the reference vehicle with PL the RWD was 2.2 times compared to Control.

FIG. 11 shows a comparison of Control, Reference Vehicle (7386)+PL and (7364/1)+PL samples after 72 h. 10× images of the samples after 72 h are presented. The black rectangle circumscribes the wound area.

Surprisingly FIG. 11 shows also a relevant difference between the example composition of the present invention and the reference formulation in terms of cells morphology and number of cells. Morphology is a key parameter to evaluate the healthy status of the cells; it was surprisingly evident that the formulation of the present invention with PL maintains the good healthy condition of the cells while in the reference vehicle with PL the images shown suffering and wrinkled cells. In fact, the cells resuspended in the formulation of the present invention with PL shown cell regular margins, while the cells resuspended in the reference vehicle with PL shown irregular margins and a reduced cytoplasm.

Figure 12:
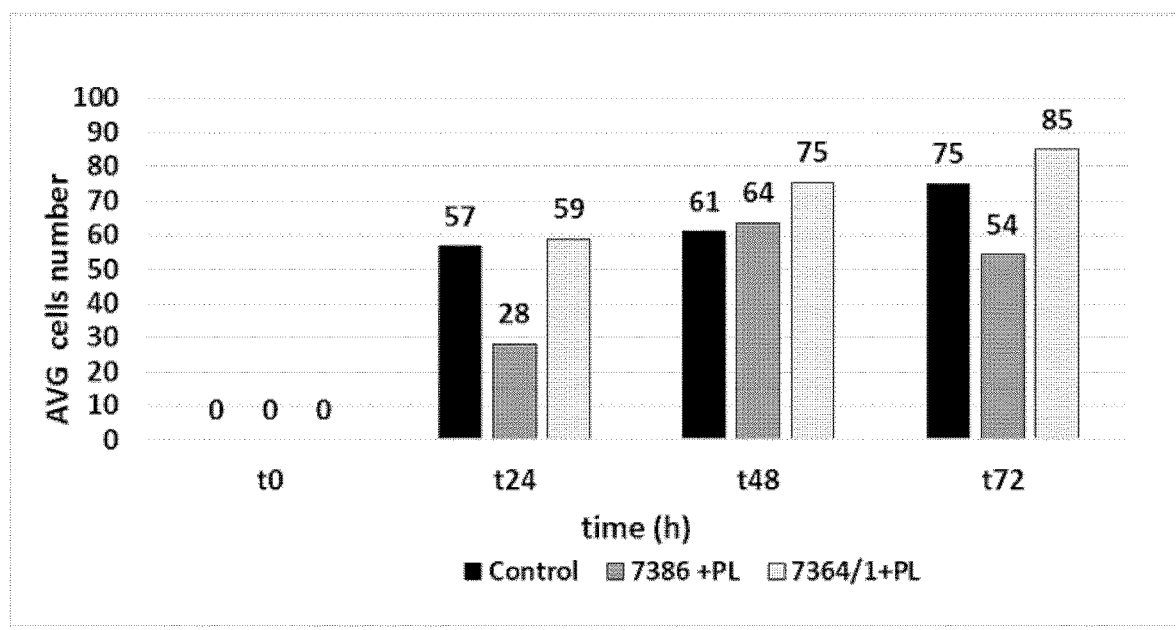
FIG. 12 shows a comparison of the average number of cells within the wound gap of Control, Reference Vehicle (7386)+PL and (7364/1)+PL samples after different time points (t0, t24, t48 and t72).

Furthermore, in terms of cells population, using ImageJ software an extrapolation was done in order to obtain the number of cells within the wound gap. FIG. 12 shows the average cell number within the wound gap for formulations under test at prefixed time points (t0, t24, t48 and t72). The example composition of the present invention with PL shows an evident increase in the average number of cells within the gap over time. It is superior to the reference vehicle with PL at all the tested time points; furthermore, it shows superiority over Control starting from 48 h.

This test demonstrates that the example formulation according to the present invention with PL shows a positive effect on cell migration and growth of the human fibroblasts up to 72 h.

In particular, thanks to this effect on cells migration and maintenance of cells morphology, the formulations of the present invention can be used as delivery vehicles for growth factors such as Platelet Lysate (PL) in wound healing and also as potential vehicles for cells and cellular material.

Example 9 Water-Based Solution

| Component(s) | % w/w |
|---|---|
| Infliximab | 0.010 |
| Gellan gum | 0.300 |
| Poloxamer 407 | 14.000 |

| Component(s) | % w/w |
| --- | --- |
| Hydroxypropylcellulose | 0.400 |
| Sodium Benzoate | 0.100 |
| Methyl p-hydroxybenzoate | 0.100 |
| Purified water up to | 100.00 |

In a suitable vessel provided with a stirrer, Purified water (95% of the total amount) is loaded; then, Sodium benzoate and Methyl para hydroxybenzoate are dissolved until complete dissolution; then the solution is cooled at a temperature ranging between 5° C. and 20° C.; then, poloxamer 407 is added under stirring. The mixture is kept under stirring until a complete dissolution is achieved and then heated up to room temperature.

Then Infliximab is added under stirring until complete dissolution is achieved.

Then Gellan gum is added to the mixture above under stirring until a homogeneous mixture is obtained.

Then Hydroxypropyl cellulose is added to the mixture above under stirring until a homogeneous mixture is achieved.

The mixture is brought to final weight adding Purified water. The mixture is kept under stirring until homogeneity is obtained. The application of such a composition can be easily done by rectal administration of the composition such as in enema, aimed to bio-adhere to the sigma and/or rectum mucosa.

Example 10 Water-Based Solution

| Component(s) | % w/w |
| --- | --- |
| Poloxamer 407 | 16.000 |
| Sodium Alginate | 0.200 |
| Collagen | 0.100 |
| Sodium Carboxymethylcellulose | 0.050 |
| WFI up to | 100.00 |

The manufacturing process of example 10 is similar to that of example 8.

The application of such a composition can be easily done by injection into the fistula lumen or in the fistula walls of a suspension of MSC for the treatment of fistulas, comprising but not limited to anal o rectovaginal fistula.

Example 11 Water-Based Solution

| Component(s) | % w/w |
| --- | --- |
| RifamycinSV | 0.060 |
| Poloxamer 188 | 22.000 |
| Sodium Alginate | 0.200 |
| Sodium Carboxymethylcellulose | 0.050 |
| WFI up to | 100.00 |

The manufacturing process of example 11 is similar to that of example 8.

The application of such a composition can be easily done by injection into the fistula lumen or in the fistula walls for the treatment of fistulas, comprising but not limited to anal o rectovaginal fistula.

Example 12 Water-Based Solution

| Component(s) | % w/w |
| --- | --- |
| *Saccharomyces Cerevisiae* | 1.000 |
| Poloxamer 407 | 20.000 |
| Sodium Alginate | 0.200 |
| Sodium Carboxymethylcellulose | 0.050 |
| WFI up to | 100.00 |

The manufacturing process of example 12 was similar to that of example 8. The composition can be applied topically to the emmorroidal plexus in form of enema or as a viscous structured composition provided with bio-adhesive properties one applied to the target mucosal tissue.

Example 13 Water-Based Solution

| Component(s) | % w/w |
| --- | --- |
| *Saccharomyces Cerevisiae* | 1.000 |
| *Aesculus Hippocastanum* | 0.200 |
| *Menta Piperita* | 0.100 |
| Poloxamer 188 | 22.000 |
| Sodium Alginate | 0.200 |
| Sodium Carboxymethylcellulose | 0.050 |
| WFI up to | 100.00 |

The manufacturing process of example 13 was similar to that of example 8.

The composition can be applied topically to the emmorroidal plexus in form of enema or as a viscous structured composition provided with bio-adhesive properties one applied to the target mucosal tissue.

Example 14

A vehicle composed by Methyl Cellulose (MC) 0.31% w/w, Gellan Gum (GG) 0.38% w/w and hydroxypropyl cellulose (HPC) 0.22% w/w is prepared. Such vehicle is intended to be applied on the mucosa of the distal colon via rectal route. The following characteristics has been considered:

1) vehicle viscosity at room temperature (25° C.), functional to an easy administration;
2) increase in vehicle viscosity after temperature increase (from room to 37° C.) and dilution with simulated colonic fluid (SCF), such an increase is functional to vehicle permanence at the application site after administration;
3) viscoelastic behavior after administration, functional to vehicle protective action at the application site.

The vehicle as is and after dilution 5:2 w/w in simulated colonic fluid (SCF) has been characterized for viscosity at increasing shear rates (10-300 s−1). SCF is prepared according to well-known conventional receipts. From viscosity data two response variables are measured:

1) viscosity of the vehicle as is at 25° C. and 50 s$^{-1}$ shear rate: 0.093±0.002 Pa·s;
2) normalized Δ viscosity at 10 s$^{-1}$: 0.7±0.2, calculated according to the following equation:

$$\text{normalized } \Delta \text{ viscosity} = (\eta_{at\ 37°\ C.\ in\ SCF} - \eta_{at\ 25°\ C.\ in\ water})/\eta_{at\ 25°\ C.\ in\ water} \quad \text{Eq 1:}$$

where $\eta_{at\ 37°\ C.\ in\ SCF}$=viscosity of the vehicle diluted in SCF (5:2 w/w ratio), measured at 37° C., 10 s$^{-1}$ shear rate;

$\eta_{at\ 25°\ C.\ in\ water}$=viscosity of the vehicle diluted in water (5:2 w/w ratio), measured at 25° C., 10 s$^{-1}$ shear rate.

In the calculation of normalized Δ viscosity at 10 s$^{-1}$, the use of the viscosity value after dilution in water measured at 25° C., instead of at 37° C., permits to point out not only the effect of ions on sample viscosity but also the effect of thermogelation (due to MC). The vehicle after 5:2 w/w dilution in SCF has been subjected to viscoelastic measurements (oscillation test) at 37° C. and to mucoadhesion characterization. Such a test provides to measure the force of detachment (Fmax) necessary to separate a vehicle layer from a filter disc soaked with a suspension of mucin in SCF. The following variables are measured:

1) as for viscoelatic measurements: loss tangent (Tan delta): 0.11±0.01, calculated as ratio between viscous (G") and elastic (G') moduli
2) as for mucoadhesion measurements: maximum force of detachment (Fmax): 1317±102 mN;

The vehicle prepared is able to gelify or to get structured when diluted in simulated colonic fluid at physiological temperature and shows mucoadhesive properties.

Example 15

A vehicle composed by Poloxamer 407 (PLX) 14.0% w/w, Gellan Gum (GG) 0.29% w/w and hydroxypropyl cellulose (HPC) 0.41% w/w is prepared. Such vehicle is intended to be applied on the mucosa of the distal colon via rectal route.

Two different dilutions with SCF are considered: 5:2 and 5:0.65 w/w. The vehicle as is and after dilution 5:2 or 5:0.65 w/w in distilled water or in SCF are characterized for viscosity at increasing shear rates (10-300 s$^{-1}$) as described in Example 16. From viscosity data 3 variables has been measured:

1) viscosity of the vehicle as is at 25° C. and 50 s$^{-1}$ shear rate: 0.206±0.001 Pa·s;
2) normalized Δ viscosity at 10 s$^{-1}$ (25° C.) when diluted 5:2 w/w=3.1±0.2 and normalized Δ viscosity at 10 s$^{-1}$ (25° C.) when diluted 5:0.65 w/w=0.9±0.05 calculated according to the following equation:

$$\text{normalized } \Delta \text{ viscosity} = (\eta_{at\ 37°\ C.\ in\ SCF} - \eta_{at\ 25°\ C.\ in\ water})/\eta_{at\ 25°\ C.\ in\ water} \quad \text{Eq 1:}$$

where $\eta_{at\ 37°\ C.\ in\ SCF}$=viscosity of the vehicle diluted in SCF (5:2 or 5:0.65 w/w ratios), measured at 37° C., 10 s$^{-1}$ shear rate;

$\eta_{at\ 25°\ C.\ in\ water}$=viscosity of the vehicle diluted in water (5:2 or 5:0.65 w/w ratios w/w ratio), measured at 25° C., 10 s$^{-1}$ shear rate.

Figure 5:
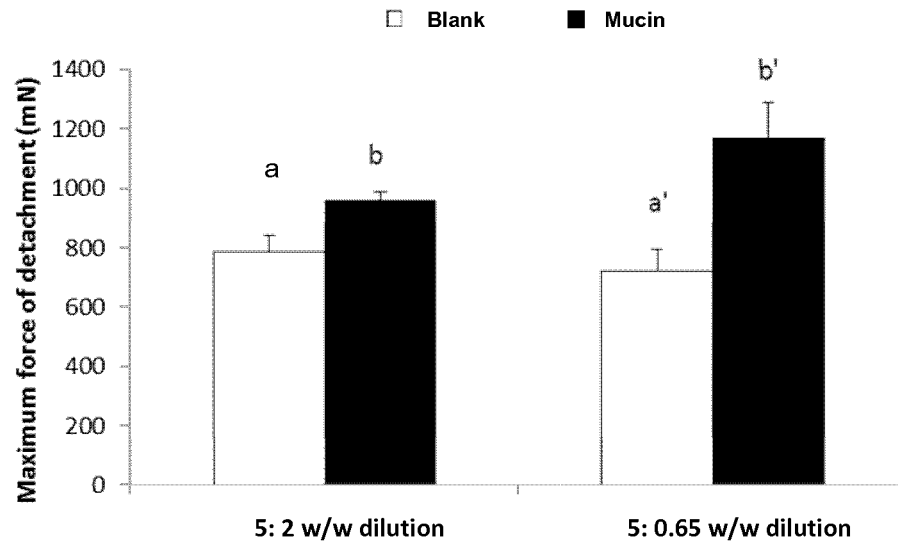
FIG. 5 shows the Fmax values obtained in presence of mucin and in absence of the biological substrate.

3) normalized Δ viscosity at 10 s$^{-1}$ (37° C.) when diluted 5:2 w/w=12.5±0.7 and normalized Δ viscosity at 10 s$^{-1}$ (37° C.) when diluted 5:0.65 w/w=1.13±0.06, calculated according to the following equation:

$$\text{normalized } \Delta \text{ viscosity} = (\eta_{at\ 37°\ C.\ in\ SCF} - \eta_{at\ 37°\ C.\ in\ water})/\eta_{at\ 37°\ C.\ in\ water} \quad \text{Eq 2:}$$

where $\eta_{at\ 37°\ C.\ in\ SCF}$=viscosity of the vehicle diluted in SCF (5:2 or 5:0.65 w/w ratios), measured at 37° C., 10 s$^{-1}$ shear rate;

$\eta_{at\ 37°\ C.\ in\ water}$=viscosity of the vehicle diluted in water (5:2 or 5:0.65 w/w ratios), measured at 37° C., 10 s$^{-1}$ shear rate;

The vehicle, diluted with SCF according to both weight ratios, also shows mucoadhesion properties. In fact, it shows higher Fmax values obtained in presence of mucin than in absence of the biological substrate (Blank) (FIG. 5).

Example 16

Figure 6:
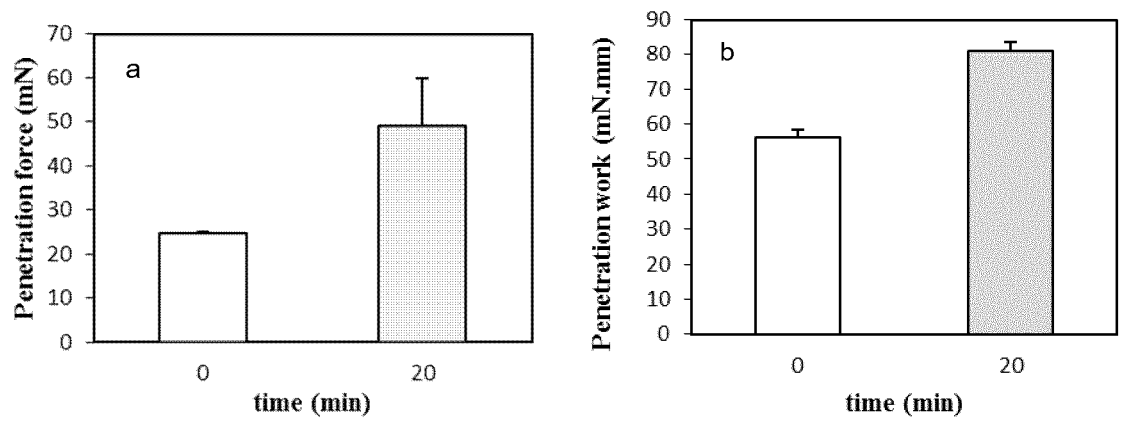
FIG. 6 (a and b) report the penetration force and work values, respectively.
Figure 7:
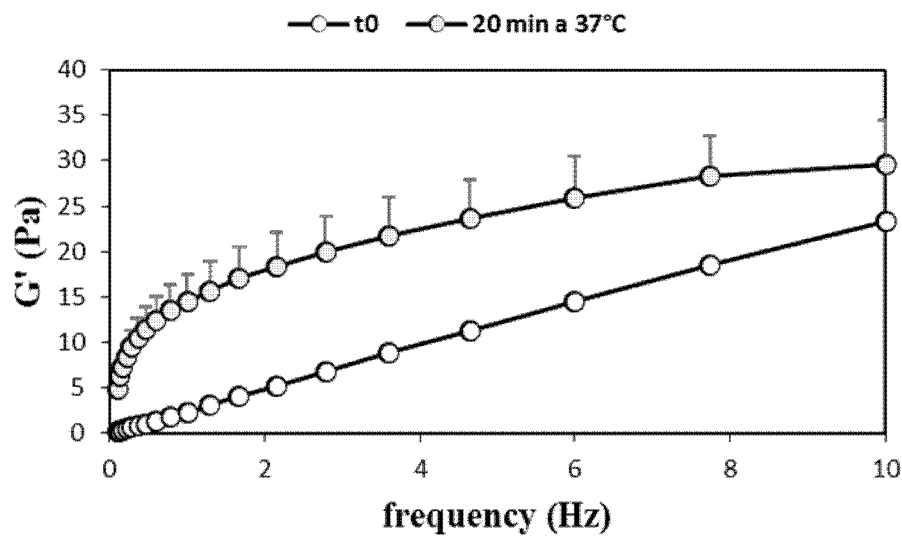
FIG. 7 shows the G' profiles indicating that after 20 min at 37° C. gelation occurs.

A vehicle intended for application on esophagus walls via oral route is prepared. The vehicle is composed by 1.5% w/w MC, 0.1% w/w sodium alginate (ALG), 2.7% w/w Sodium Bicarbonate (NaHCO$_3$), 0.3% w/w Magnesium Oxide (MgO). It is prepared by dissolving MC in distilled water under stirring at 90° C. at 3% w/w concentration. Subsequently the solution is placed in an ice bath under stirring until it becomes completely transparent. MC solution is mixed 1:1 w/w with an aqueous solution of 0.2% w/w ALG and 5.4% w/w NaHCO$_3$. Finally, MgO is added. After thermo-statation at 37° C. for 20 min the vehicle shows an increased consistency. Such an increase is assessed by penetrometry and viscoelastic measurements. Penetrometry test is performed at room temperature and after thermostatation at 37° C. for 20 min. FIG. 6 (a and b) reports the penetration force and work values, respectively. Viscoelastic measurement is performed at 25° C. and after thermostatation at 37° C. for 20 min. Sample elasticity, expressed by the storage elastic modulus (G'), is measured at frequency values increasing into the range 0.1-10 Hz. FIG. 7 shows vehicle G' profiles. The results obtained indicate that after 20 min thermostatation at 37° C. vehicle gelation occurs.

Figure 8:
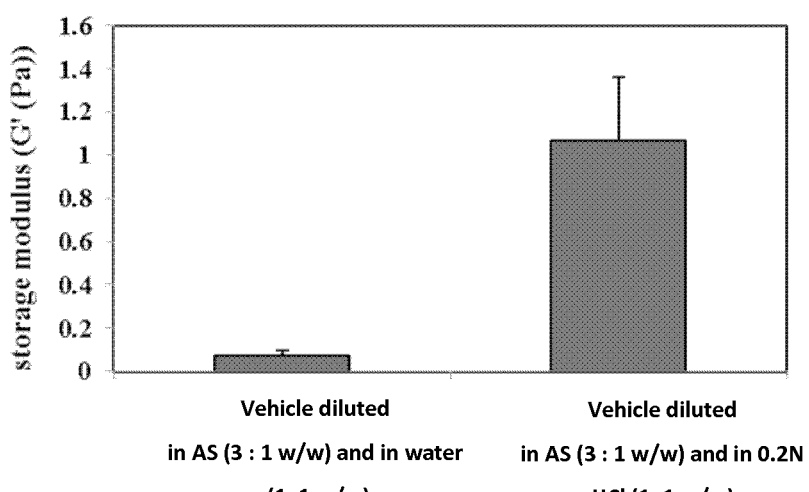
FIG. 8 reports the elastic modulus value (G') of the vehicle after double dilution.

The vehicle performance is investigated after a double dilution: 3:1 w/w in artificial saliva (AS) and 1:1 w/w in HCl 0.2 N, to mimic the in vivo situation. FIG. 8 reports the elastic modulus (G') of the vehicle after the above mentioned double dilution. G' value of the vehicle diluted 3:1 w/w in AS and 1:1 in water instead of HCl is used as reference to investigate the effect of an acidic environment on vehicle performance. The results obtained prove that the elasticity of the vehicle, functional to a protective action towards esophageous walls, increases after dilution in HCl.

Example 17

Two different vehicles were prepared:
1) a vehicle containing a water solution of Poloxamer 407 10.3% w/w and
2) a vehicle containing a mixture of Poloxamer 407 10.3% w/w and Gellan gum 0.41% w/w in purified water.

Both vehicles were characterized for elastic modulus G' upon dilution in water or in Simulated Colonic Fluid according to 5:2 w/w ratio. The values of the differential parameter ΔG', calculated as the difference between G' values observed at the physiological temperature (36, 38° C.) and at room temperature (25° C.), upon dilution 5:2 w/w with purified water, were calculated and reported in Table 3. It can be observed that the presence of the ion-sensitive polymer, GG, surprisingly generates a marked increase in such parameter, indicating a strengthening of the gel formed.

Figure 9:
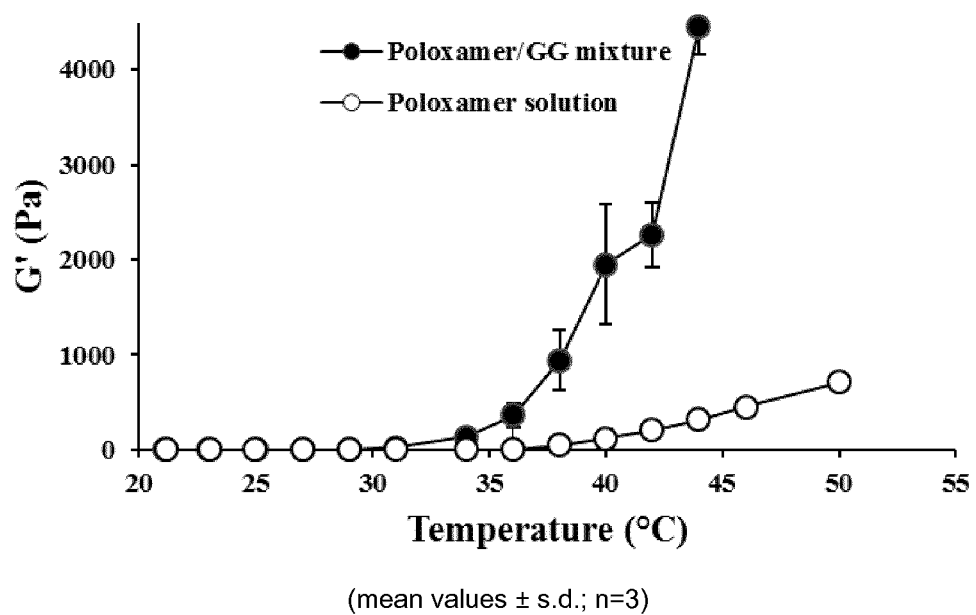
FIG. 9 shows the improvement of the strength of a gel based on Poloxamer (Kolliphor® P407) in the physiological range of temperature upon addition of gellan gum (GG).

It is even more surprisingly found a further increase in gel strength when the same samples are diluted in simulated colonic fluid 5:2 w/w ratio) (FIG. 9; Table 4).

Table 3—Values of the differential parameter ΔG' calculated for a Poloxamer solution (10.3% w/w Poloxamer diluted 5:2 w/w in distilled water) and for a Poloxamer/GG mixture (10.3% w/w Poloxamer/0.41% w/w GG, diluted 5:2 w/w in distilled water) (mean values±s.e., n=3)

$$\Delta G'_{36\ or\ 38°\ C.} = (G'_{36\ or\ 38°\ C.} - G'_{25°\ C.})$$

| SAMPLES | ΔG'$_{36° C.}$ (Pa) | ΔG'$_{38° C.}$ (Pa) |
| --- | --- | --- |
| Poloxamer solution | 0.6 ± 0.2 | 52 ± 15 |
| Poloxamer/GG mixture | 362 ± 90 | 940 ± 222 |

Table 4—Values of the differential parameter ΔG' calculated for a Poloxamer solution (10.3% w/w Poloxamer, diluted 5:2 w/w in simulated colonic fluid) and for a Poloxamer/GG mixture (10.3% w/w Poloxamer/0.41% w/w GG, diluted 5:2 w/w in simulated colonic fluid) (mean values±s.e., n=3)

$$\Delta G'_{36 \text{ or } 38° C.} = (G'_{36 \text{ or } 38° C.} - G'_{25° C.})$$

| SAMPLES | ΔG'$_{36° C.}$ (Pa) | ΔG'$_{38° C.}$ (Pa) |
| --- | --- | --- |
| Poloxamer solution | 598 ± 149 | 1050 ± 267 |
| Poloxamer/GG mixture | 2162 ± 93 | 4937 ± 1129 |

It is therefore surprisingly shown that at 37° C. the elastic modulus G' significantly increases when the thermo-responsive polymer is combined with the ion-sensitive polymer. This is even more surprisingly found when the combination of the invention (thermos-responsive+ion-sensitive) is diluted with the simulated colonic fluid mimicking the intestinal real environment (about 37° C. body temperature in water only is 940±222 Pa versus simulated colonic fluid which is 4937±1129 Pa).

The invention claimed is:

1. A composition for use as a delivery vehicle comprising at least one thermo-responsive polymer, at least one ion-sensitive polymer, and at least one bio-adhesive polymer in a liquid formulation, wherein the at least one thermo-responsive polymer comprises 0.3-25% (w/w) poloxamer 407, the at least one ion-sensitive polymer comprises 0.01-2.0% (w/w) sodium alginate, and the at least one bio-adhesive polymer comprises 0.01-2.0% (w/w) sodium carboxymethylcellulose, wherein the composition comprises at least one active substance for delivery, wherein the at least one active substance comprises: monoclonal antibodies, anti-acids, adrenergic drugs, anti-adrenergic drugs, dyes, steroidal and non-steroidal anti-inflammatory drugs, nasal antihistamines, nasal decongestants, anti-neoplastics, antimicrobics, antibiotics, antifungal drugs, genitourinary tract agents, vaginal agents, vaginal antifungal, vaginal antibiotics, oral cavity disinfectants or oral cavity antibiotics, wound healing drugs, haemostatics, anaesthetics, or a mixture thereof;
wherein the composition is formulated such that an active substance can be added at the time of administration.

2. A composition as claimed in claim 1, further comprising at least one excipient selected from the group consisting of antioxidants, chelating agents, preservatives, antimicrobial agents, surfactants, co-surfactants, lipophilic compounds, purified water or water for injection, organic and inorganic salts, and buffer agents having trophic activity.

3. A composition as claimed in claim 1, wherein the at least one active substance further comprises cellular material comprising microvesicles, genomic material, or lysosomes; differentiated cells derived from ectoderm, endoderm or mesoderm; or stem cells comprising embryonic stem cells, tissue-specific stem cells, mesenchymal stem cells; or induced pluripotent stem cells.

4. A composition as claimed in claim 1, wherein the composition is administered by oral, buccal, ocular, rectal, perianal, vaginal, ear, nasal, dental route or by injection.

5. A composition as claimed in claim 1, wherein the composition is formulated as a formulation selected from the group consisting of a solution, a micellar dispersion, a suspension, an emulsion, a micro-emulsion, enema, syrup, drop, structured viscous composition, vaginal douche, and liquid in soft gel capsules.

6. A method of medical treatment comprising the administration of a composition as claimed in claim 1.

7. A composition as claimed in claim 1, wherein poloxamer 407 is present in an amount of 15% (w/w) with respect to the weight of the composition.

8. A composition as claimed in claim 1, wherein sodium alginate is present in an amount of 0.2% (w/w) with respect to the weight of the composition.

9. A composition as claimed in claim 7, wherein sodium carboxymethylcellulose is present in an amount of 0.05% (w/w) with respect to the weight of the composition.

10. A composition as claimed in claim 1, wherein the at least one active substance administration further comprises human skin fibroblasts.

11. A composition as claimed in claim 1, wherein the composition is administered by injection, wherein the injection route of administration is sub-mucosal, intraperitoneal, intra-tumoral, sub-cutaneous, intramuscular, intraarticular, intranasal, perianal intrathecal, epidural or, intra-parenchymal to the brain or spinal cord or to sub-retinal spaces.

* * * * *